US008426040B2

(12) United States Patent
Zheng et al.

(10) Patent No.: US 8,426,040 B2
(45) Date of Patent: *Apr. 23, 2013

(54) COMPOUNDS FOR USE IN LIGHT-EMITTING DEVICES

(75) Inventors: Shijun Zheng, San Diego, CA (US);
Liping Ma, San Diego, CA (US);
Amane Mochizuki, Carlsbad, CA (US)

(73) Assignee: Nitto Denko Corporation, Osaka (JP)

( * ) Notice: Subject to any disclaimer, the term of this patent is extended or adjusted under 35 U.S.C. 154(b) by 38 days.

This patent is subject to a terminal disclaimer.

(21) Appl. No.: 13/033,473

(22) Filed: Feb. 23, 2011

(65) Prior Publication Data
US 2011/0140093 A1 Jun. 16, 2011

Related U.S. Application Data

(60) Provisional application No. 61/426,259, filed on Dec. 22, 2010.

(51) Int. Cl.
*H01L 51/54* (2006.01)
*C09K 11/06* (2006.01)

(52) U.S. Cl.
USPC .......................... 428/690; 428/917; 313/504

(58) Field of Classification Search ................ 548/310.7
See application file for complete search history.

(56) References Cited

U.S. PATENT DOCUMENTS

| 6,232,322 | B1 | 5/2001 | Malamas et al. | |
| 6,620,529 | B1 * | 9/2003 | Ise et al. | 428/690 |
| 6,835,469 | B2 * | 12/2004 | Kwong et al. | 428/690 |
| 7,851,074 | B2 | 12/2010 | Kido et al. | |
| 2008/0014464 | A1 * | 1/2008 | Kawamura et al. | 428/690 |
| 2009/0134783 | A1 | 5/2009 | Lin et al. | |
| 2010/0060154 | A1 | 3/2010 | Nomura et al. | |
| 2010/0308716 | A1 | 12/2010 | Zheng | |
| 2010/0326526 | A1 | 12/2010 | Zheng et al. | |
| 2010/0327269 | A1 | 12/2010 | Zheng et al. | |
| 2011/0140093 | A1 | 6/2011 | Zheng et al. | |
| 2011/0251401 | A1 | 10/2011 | Zheng et al. | |

FOREIGN PATENT DOCUMENTS

| EP | 0 499 222 | 2/1992 |
| JP | 64-009959 | 1/1989 |
| JP | 7-076542 A | 3/1995 |
| JP | 7207169 | 8/1995 |
| KR | 959189 B1 | 5/2010 |
| WO | WO 99/58518 A2 | 11/1999 |
| WO | WO 2004010996 | 2/2004 |
| WO | WO 2004/020388 | 3/2004 |
| WO | WO 2010/044607 | 4/2010 |
| WO | WO 2011/008560 | 1/2011 |

OTHER PUBLICATIONS

Chen et al., "Versatile Benzimidazole/Amine-Based Ambipolar Compounds for Electroluminescent Applications: Single-Layer, Blue, Fluorescent OLEDs, Hosts for Single-Layer, Phosphorescent OLEDs" Advanced Functional Materials, vol. 19, No. 16, Aug. 24, 2009, pp. 2661-2670.
International Search Report and Written Opinion for International Application No. PCT/US2011/066536, mailed on Mar. 1, 2012 in 14 pages.
Li et al., "Synthesis and Functional Properties of Strongly Luminescent Diphenylamino End-Capped Oligophenylenes" Journal of Organic Chemistry, American Chemical Society, vol. 69, No. 3, pp. 921-927, Feb. 6, 2004.
Copending U.S. Appl. No. 12/826,589, filed Jun. 29, 2010.
Ge, Ziyi et al., "Solution-Processible Bipolar Triphenylamine-Benzimidazole Derivatives for Highly Efficient Single-Layer Organic Light-Emitting Diodes", Chemistry of Materials, 20 (7), 2532-2537, XP002608601, published on Web Mar. 11, 2008.
Ge, Ziyi et al., "Spin-Coated Highly Efficient Phosphorescent Organic Light-Emitting Diodes Based on Bipolar Triphenylamine-Benzimidazole Derivatives", Advanced Functional Materials, vol. 18, No. 4, Feb. 22, 2008, pp. 584-590, XP001510816, Wiley, ISSN:1616-301X.
Kauffman, et al., Synthesis and photophysical properties of fluorescent 2-aryl-1,3-dialkylbenzimidazolium ions and a 1-alkyl-2-arylbenzimidazole with excited state intramolecular proton-transfer. Journal of Heterocyclic Chemistry (1994), 31(4), 957-65.
Malamas, et al., Novel Benzofuran and Benzothiophene Biphenyls as Inhibitors of Protein Tyrosine Phosphatase 1B with Antihyperglycemic Properties. Journal of Medicinal Chemistry (2000), 43(7), 1293-1310.
Ueda, et al., Synthesis of poly(benzothiazole)s by direct polycondensation of dicarboxylic acids with 2,5-diamino-1,4-benzenedithiol dihydrochloride using phosphorus pentoxide/methaneusulfonic acid as condensing agent and solvent, Polymer Journal vol. 18, No. 2, 1986 pp. 117-122, (abstract only).
Vinodkumar, et al., Synthesis of highly functionalized 2-(substituted biphenyl)benzimidazoles via Suzuki-Miyaura cross-coupling reaction. Journal of Heterocyclic Chemistry (2007), 44(6), 1521-1523.
HCAPLUS AN 1999:812802, abstract for Kim et al., "Synthesis and properties of highly fluorescent liquid crystals containing benzoxazole moiety", Molecular Crystals and Liquid Crystals Science and Technology, Section A, No. 337, pp. 405-408 (1999).

* cited by examiner

*Primary Examiner* — Marie R. Yamnitzky
(74) *Attorney, Agent, or Firm* — K&L Gates LLP; Louis C. Cullman; Brent A. Johnson

(57) ABSTRACT

Compounds including optionally substituted Ring Systems 1-4 are described. These compounds may be used as hosts in light-emitting devices. A light-emitting device comprising a compound selected from optionally substituted Ring Systems 1-4 is also described. The Ring Systems 1-4 are:

(Ring system 1)

-continued
(Ring system 2)
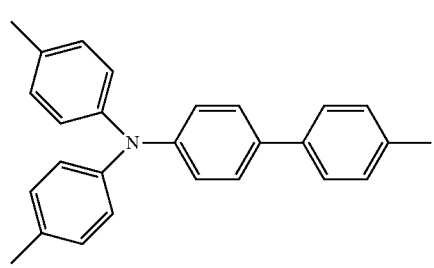
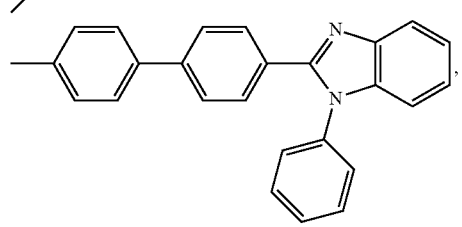,
(Ring system 3)
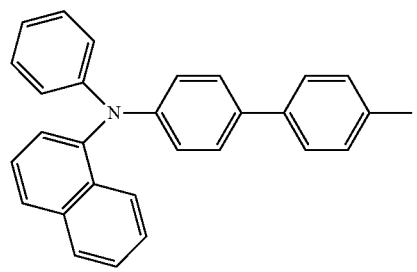
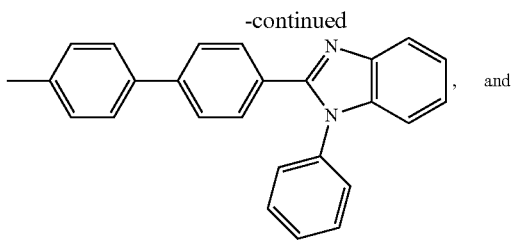, and
(Ring system 4)
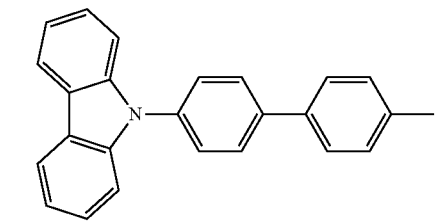
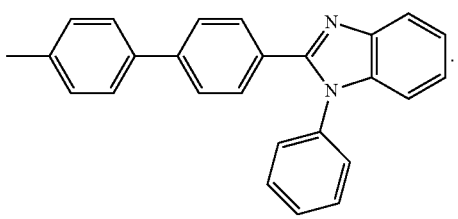.
3 Claims, 10 Drawing Sheets

COMPOUNDS FOR USE IN LIGHT-EMITTING DEVICES

CROSS-REFERENCE TO RELATED APPLICATIONS

This application claims the benefit of U.S. Provisional Application No. 61/426,259, filed Dec. 22, 2010, which is incorporated by reference herein in its entirety.

BACKGROUND

1. Field

The embodiments include compounds for use in light-emitting devices.

2. Description of the Related Art

Organic light-emitting devices have been widely developed for flat panel displays, and are moving fast toward solid state lighting (SSL) applications. Continued development of new compounds for improvement of efficiency and/or lifetimes of these devices is needed to realize the full commercial potential of these devices.

SUMMARY

Some embodiments include compounds comprising an optionally substituted ring system selected from the group consisting of:

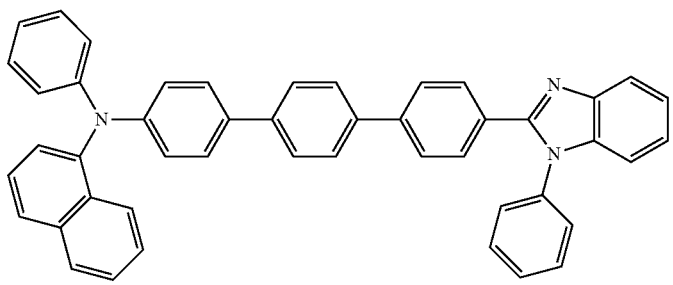

(Ring system 1)

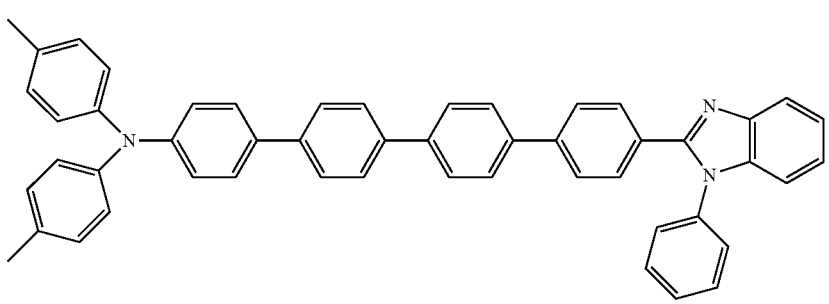

(Ring system 2)

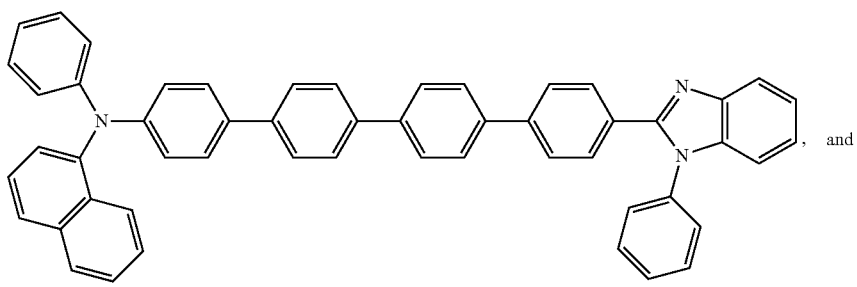

(Ring system 3)

, and

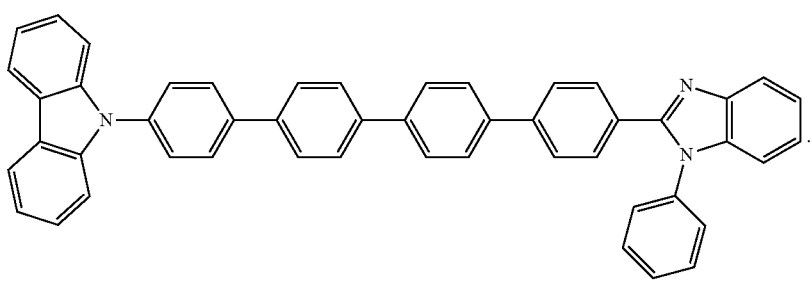

(Ring system 4)

.

Some embodiments include light-emitting devices comprising a compound described herein.

DETAILED DESCRIPTION

Figure 1:
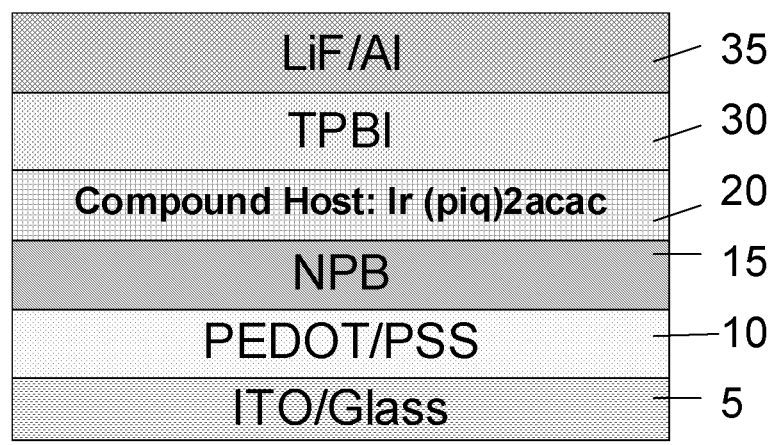
FIG. 1 is a schematic diagram of an embodiment of a device described herein.
Figure 2:
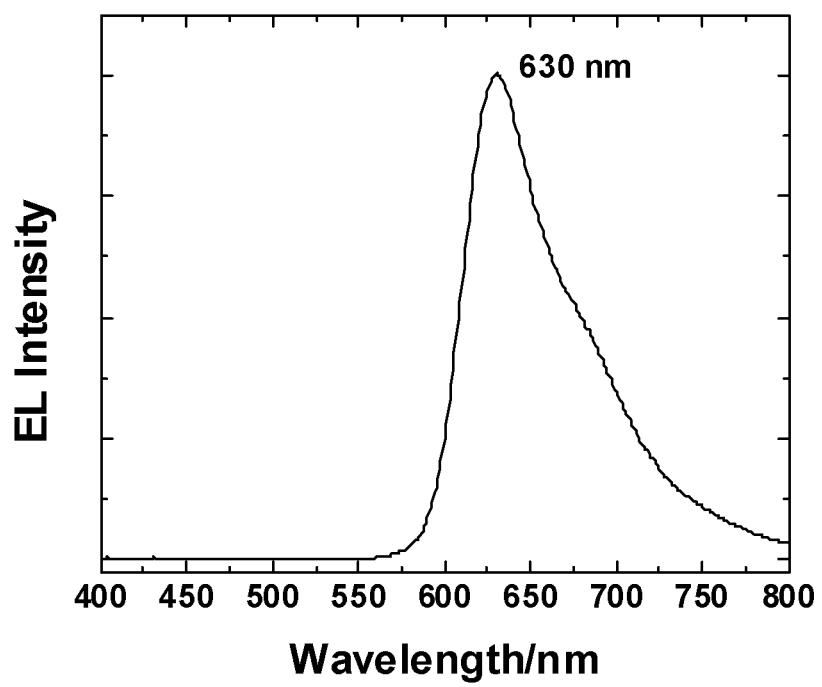
FIG. 2 is the electroluminescence spectrum of an embodiment of a light emitting device.
Figure 3:
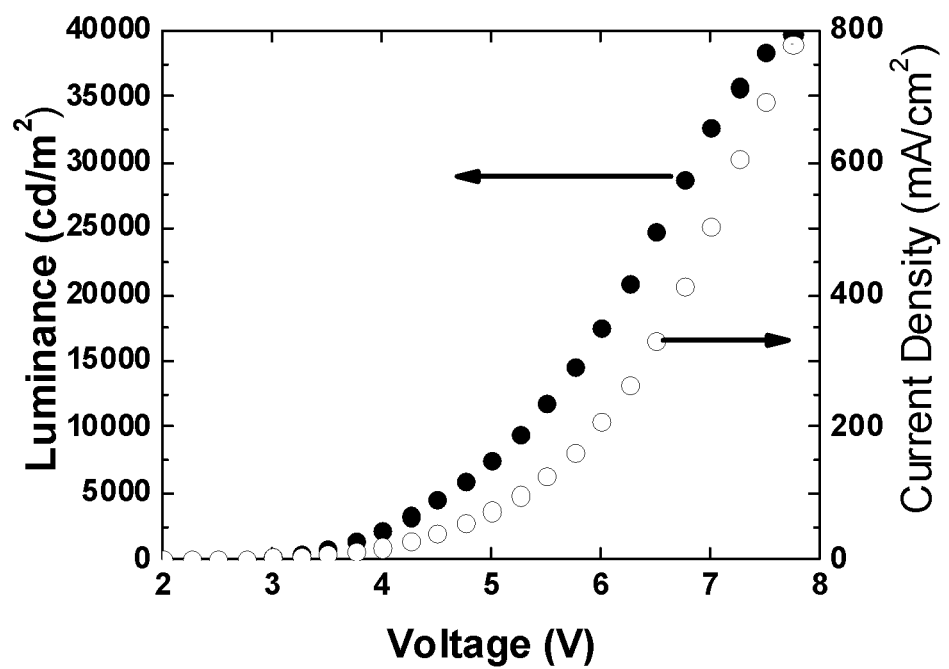
FIG. 3 is a current density/brightness vs. voltage curve of an embodiment of a light emitting device.
Figure 4:
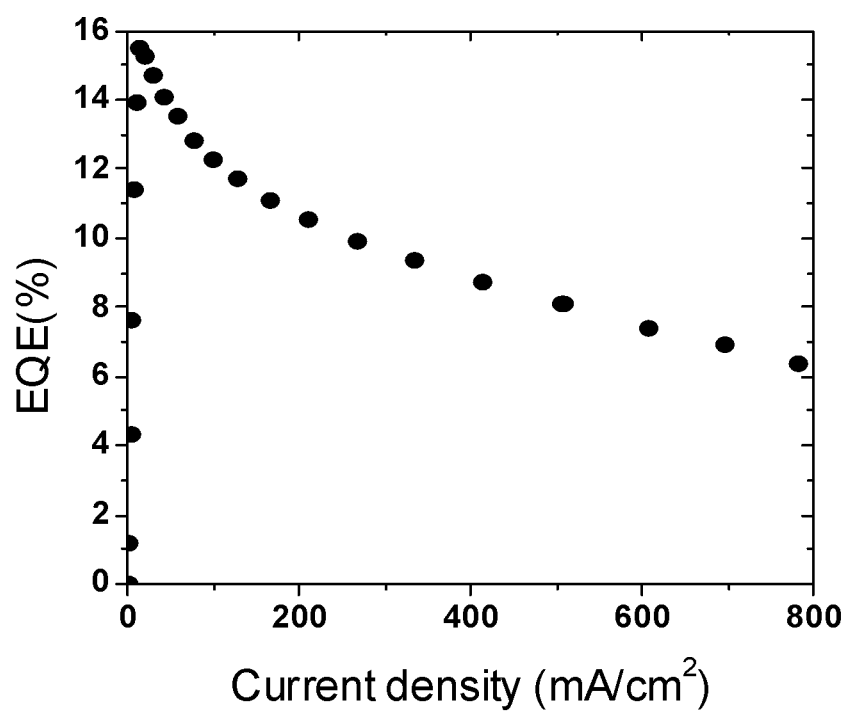
FIG. 4 shows the EQE (external quantum efficiency) with respect to the current density of an embodiment of a light-emitting device.
Figure 5:
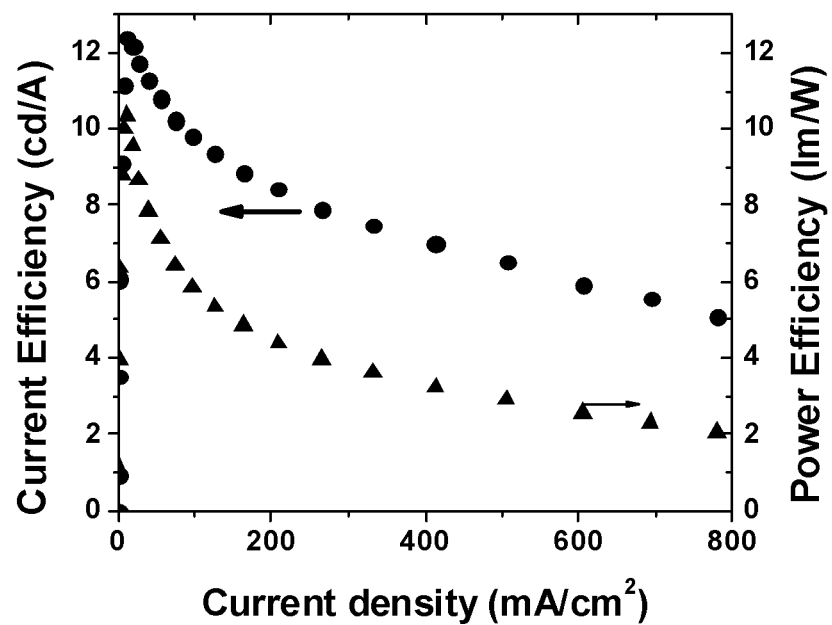
FIG. 5 is a plot of current efficiency/power efficiency vs. current density of an embodiment of a light emitting device.
Figure 6:
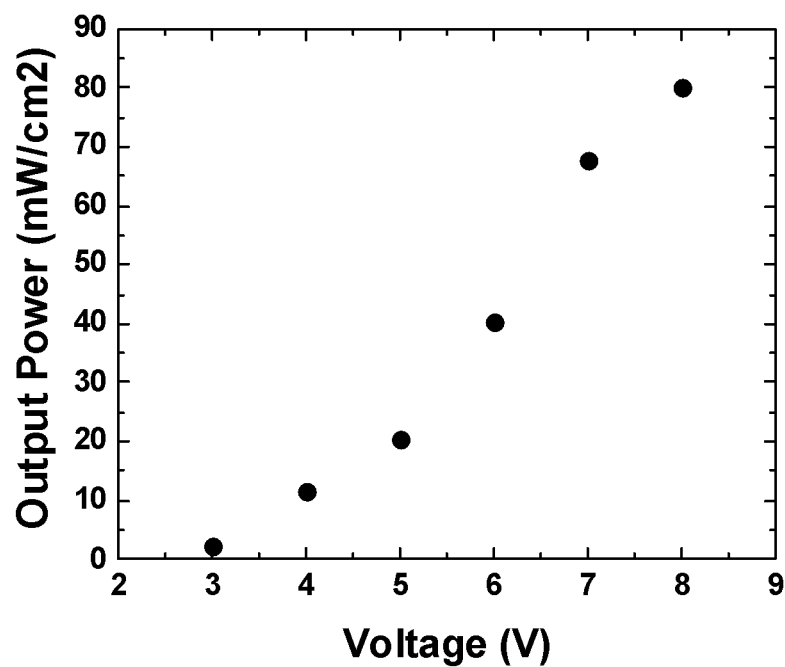
FIG. 6 is a plot of power output vs. voltage of an embodiment of a light emitting device.

Unless otherwise indicated, when a chemical structural feature such as aryl is referred to as being "optionally substituted," it is meant that the feature may have no substituents (i.e. be unsubstituted) or may have one or more substituents. A feature that is "substituted" has one or more substituents. The term "substituent" has the ordinary meaning known to one of ordinary skill in the art. In some embodiments, the substituent is a halogen, or has from 1-20 carbon atoms, from 1-10 carbon atoms, or has a molecular weight of less than about 500, about 300, or about 200. In some embodiments, the substituent has at least 1 carbon atom or at least 1 heteroatom, and has about 0-10 carbon atoms and about 0-5 heteroatoms independently selected from: N, O, S, F, Cl, Br, I, and combinations thereof. In some embodiments, each substituent consists of about 0-20 carbon atoms, about 0-47 hydrogen atoms, about 0-5 oxygen atoms, about 0-2 sulfur atoms, about 0-3 nitrogen atoms, about 0-1 silicon atoms, about 0-7 fluorine atoms, about 0-3 chlorine atoms, about 0-3 bromine atoms, and about 0-3 iodine atoms. Examples include, but are not limited to, alkyl, alkenyl, alkynyl, carbazolyl, cycloalkyl, cycloalkenyl, cycloalkynyl, aryl, diarylamino, heteroaryl, heteroalicyclyl, aralkyl, heteroaralkyl, (heteroalicyclyl)alkyl, hydroxy, protected hydroxy, alkoxy, aryloxy, acyl, ester, mercapto, alkylthio, arylthio, cyano, halogen, carbonyl, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, haloalkoxyl, trihalomethanesulfonyl, trihalomethanesulfonamido, and amino, including mono- and di-substituted amino groups, and the protected derivatives thereof.

In some embodiments, the substituents may include, but are not limited to, $C_{1-10}$ alkyl such as methyl, ethyl, propyl isomers (e.g. n-propyl and isopropyl), cyclopropyl, butyl isomers, cyclobutyl isomers (e.g. cyclobutyl, methylcyclopropyl, etc.), pentyl isomers, cyclopentyl isomers, hexyl isomers, cyclohexyl isomers, heptyl isomer, cycloheptyl isomers, etc; alkoxy such as —$OCH_3$, —$OC_2H_5$, —$OC_3H_7$, —$OC_4H_9$, —$OC_5H_{11}$, —$OC_6H_{13}$, —$OC_7H_{15}$, etc.; halo, such as F, Cl, Br, I, etc.; $C_{1-10}$ haloalkyl, including perfluoroalkyl such as —$CF_3$, —$C_2F_5$, —$C_3F_7$, —$C_4F_9$, etc.; $C_{1-10}$ acyl such as formyl, acetyl, benzoyl, etc.; $C_{1-10}$ amides attaching at the carbonyl or nitrogen atom such as —$NCOCH_3$, —$CONHCH_2$, etc.; $C_{1-10}$ esters attaching at the carbonyl or oxygen atom such as —$OCOCH_3$, —$CO_2CH_2$, etc.; $C_{1-10}$ carbamates attaching at the nitrogen atom or oxygen atom; cyano; cyanate; isocyanate; nitro; etc.

In some embodiments, the substituents may be selected from: F, Cl, $C_{1-6}$ alkyl, —O—$C_{1-6}$ alkyl, CN, $NO_2$, and $CF_3$.

In some embodiments, the compounds may consist essentially of: a Ring system 1, Ring system 2, Ring system 3, or Ring system 4, each without substituents, or Ring system 1, Ring system 2, Ring system 3, or Ring system 4, each with one or more substituents on the ring system. In some embodiments, Ring system 1, Ring system 2, Ring system 3, or Ring system 4 may each have 1, 2, 3, 4, 5, 6, 7, 8, 9, or 10 substituents.

The compounds and compositions described herein can be incorporated into light-emitting devices in various ways. For example, an embodiment provides an organic component disposed between an anode and a cathode. In some embodiments, the device may be configured so that holes can be transferred from the anode to the organic component. In some embodiments, the device may be configured so that electrons can be transferred from the cathode to the organic component. The organic component may comprise the compounds and/or compositions described herein.

The anode may be a layer comprising a conventional material such as a metal, mixed metal, alloy, metal oxide or mixed-metal oxide, conductive polymer, and/or an inorganic material such as carbon nanotube (CNT). Examples of suitable metals include the Group 1 metals, the metals in Groups 4, 5, 6, and the Group 8-10 transition metals. If the anode layer is to be light-transmitting, metals in Group 10 and 11, such as Au, Pt, and Ag, or alloys thereof; or mixed-metal oxides of Group 12, 13, and 14 metals, such as indium-tin-oxide (ITO), indium-zinc-oxide (IZO), and the like, may be used. In some embodiments, the anode layer may be an organic material such as polyaniline. The use of polyaniline is described in "Flexible light-emitting diodes made from soluble conducting polymer," Nature, vol. 357, pp. 477-479 (11 Jun. 1992). Examples of suitable high work function metals and metal oxides include but are not limited to Au, Pt, or alloys thereof; ITO; IZO; and the like. In some embodiments, the anode layer can have a thickness in the range of about 1 nm to about 1000 nm.

A cathode may be a layer including a material having a lower work function than the anode layer. Examples of suitable materials for the cathode layer include those selected from alkali metals of Group 1, Group 2 metals, Group 12 metals including rare earth elements, lanthanides and actinides, materials such as aluminum, indium, calcium, barium, samarium and magnesium, and combinations thereof. Li-containing organometallic compounds, LiF, and $Li_2O$ may also be deposited between the organic layer and the cathode layer to lower the operating voltage. Suitable low work function metals include but are not limited to Al, Ag, Mg, Ca, Cu, Mg/Ag, LiF/Al, CsF, CsF/Al or alloys thereof. In some embodiments, the cathode layer can have a thickness in the range of about 1 nm to about 1000 nm.

In some embodiments, the organic component may comprise at least one light-emitting layer comprising a light-emitting component, and optionally, a host. A host may comprise a compound described herein, a hole-transport material, an electron-transport material, and/or an ambipolar material. In some embodiments, the device may be configured so that holes can be transferred from the anode to the light-emitting layer. In some embodiments, the device may be configured so that electrons can be transferred from the cathode to the light-emitting layer. If present, the amount of the host in a light-emitting layer can vary. In one embodiment, the amount of a host in a light-emitting layer may be in the range of from about 1% to about 99.9% by weight of the light-emitting layer. In another embodiment, the amount of a host in a light-emitting layer may be in the range of from about 90% to about 99% by weight of the light-emitting layer. In another embodiment, the amount of a host in a light-emitting layer may be about 97% by weight of the light-emitting layer.

In some embodiments, the mass of the light-emitting component may be about 0.1% to about 10%, about 1% to about 5%, or about 3% of the mass of the light-emitting layer. In some embodiments, the light-emitting layer may be a neat light-emitting layer, meaning that the light-emitting component is about 100% by weight of the light-emitting layer, or alternatively, the light-emitting layer consists essentially of light-emitting component. The light-emitting component may be a fluorescent and/or a phosphorescent compound. In some embodiments, the light-emitting component comprises a phosphorescent material.

The light-emitting component or compound may be chosen to vary the color of the light emitted by the light-emitting device. For example, a blue light-emitting component may emit a combination of visible photons so that the light appears to have a blue quality to an observer. In some embodiments, a blue light-emitting component may emit visible photons having an average wavelength in the range of about 440 nm or about 460 nm to about 490 nm or about 500 nm. The "average wavelength" of visible photons may include, when referring to the visible emission spectrum of a compound, the wavelength wherein the area under the curve for the part of the visible spectrum having a lower wavelength than the average wavelength is about equal to the area under the curve for the part of the visible spectrum having a higher wavelength than the average wavelength. Some non-limiting examples of compounds which may form part or all of a blue light-emitting component include iridium coordination compounds such as: bis-{2-[3,5-bis(trifluoromethyl)phenyl]pyridinato-N,C2'}iridium (III)-picolinate, bis(2-[4,6-difluorophenyl]pyridinato-N,C2')iridium (III) picolinate, bis(2-[4,6-difluorophenyl]pyridinato-N,C2')iridium(acetylacetonate), Iridium (III) bis(4,6-difluorophenylpyridinato)-3-(trifluoromethyl)-5-(pyridine-2-yl)-1,2,4-triazolate, Iridium (III) bis(4,6-difluorophenylpyridinato)-5-(pyridine-2-yl)-1H-tetrazolate, bis[2-(4,6-difluorophenyl)pyridinato-N,C$^{2'}$]iridium (III)tetra(1-pyrazolyl)borate, etc.

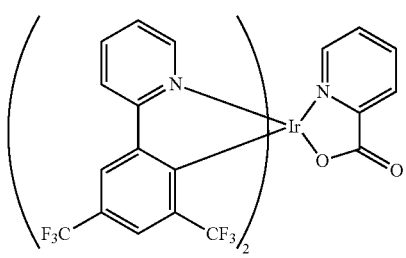

bis-{2-[3,5-bis(trifluoromethyl)phenyl]pyridinato-N,C2'}iridium(III)-picolinate
(Ir(CF$_3$ppy)$_2$(Pic))

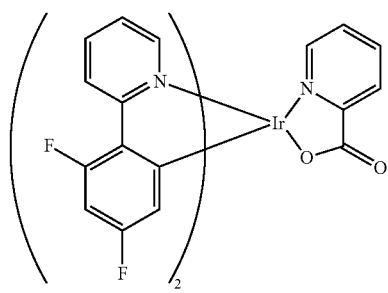

bis(2-[4,6-difluorophenyl]pyridinato-N,C2')iridium (III) picolinate [FIrPic]

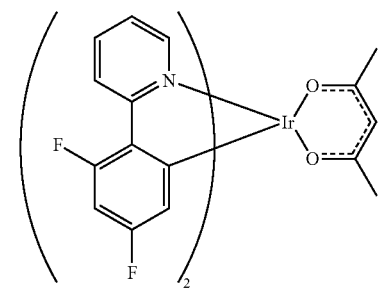

bis(2-[4,6-difluorophenyl]pyridinato-N,C2')iridium(acetylacetonate) [FIr(acac)]

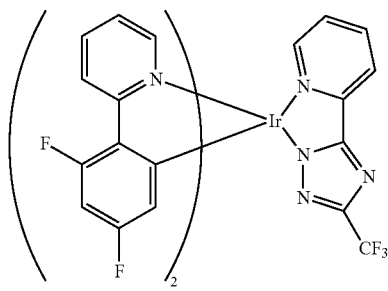

Iridium (III) bis(4,6-difluorophenylpyridinato)-3-(trifluoromethyl)-5-(pyridine-2-yl)-1,2,4-triazolate (FIrtaz)

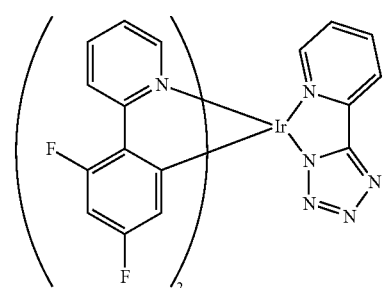

Iridium (III) bis(4,6-difluorophenylpyridinato)-5-(pyridine-2-yl)-1H-tetrazolate (FIrN4)

bis[2-(4,6-difluorophenyl)pyridinato-
N,C2']iridium(III)tetra(1-pyrazolyl)borate (Fir6)

A red light-emitting component may emit a combination of visible photons so that the light appears to have a red quality to an observer. In some embodiments, a red light-emitting component may emit visible photons having an average wavelength in the range of about 600 nm, about 620 nm, or 651 nm, to about 780 nm or about 800 nm. Some non-limiting examples of compounds which may form part or all of a red light-emitting component include iridium coordination compounds such as: Bis[2-(2'-benzothienyl)-pyridinato-N,C3'] iridium (III)(acetylacetonate); Bis[(2-phenylquinolyl)-N, C2']iridium (III) (acetylacetonate); Bis[(1-phenylisoquinolinato-N,C2')]iridium (III) (acetylacetonate); Bis[(dibenzo[f, h]quinoxalino-N,C2')iridium (III)(acetylacetonate); Tris(2,5-bis-2'-(9',9'-dihexylfluorene)pyridine)iridium (III); Tris[1-phenylisoquinolinato-N,C2']iridium (III); Tris-[2-(2'-benzothienyl)-pyridinato-N,C3']iridium (III); Tris[1-thiophen-2-ylisoquinolinato-N,C3']iridium (III); and Tris[1-(9,9-dimethyl-9H-fluoren-2-yl)isoquinolinato-(N, C3')iridium (III)), etc.

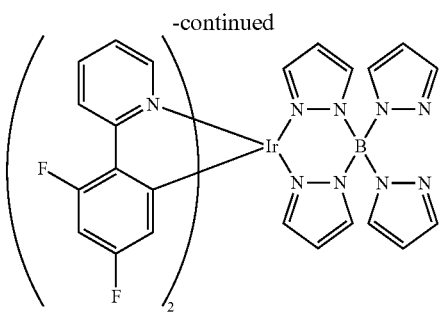

Ir(btp)₂(acac)

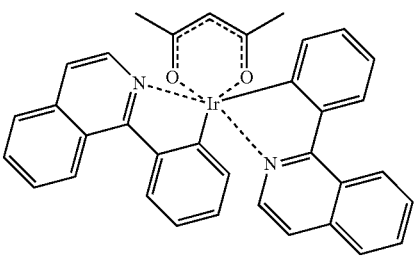

Ir(pq)₂(acac)

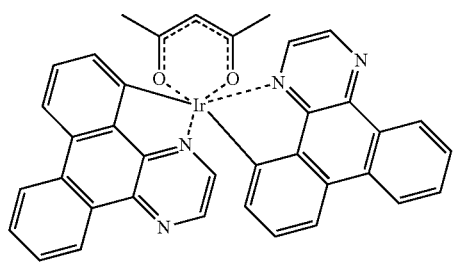

Ir(piq)₂(acac)

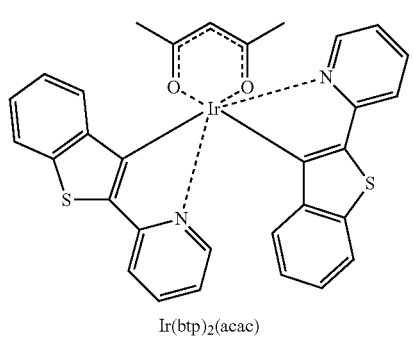

Ir(DBQ)₂(acac)

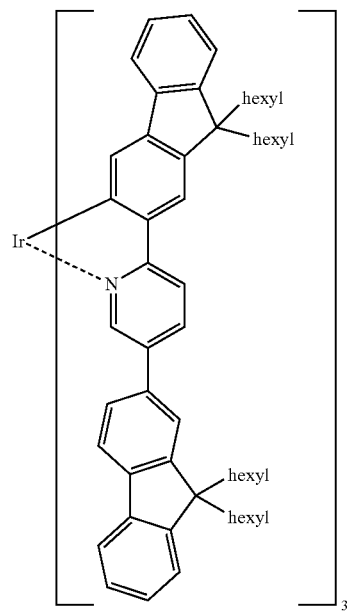

Ir(HFP)₃

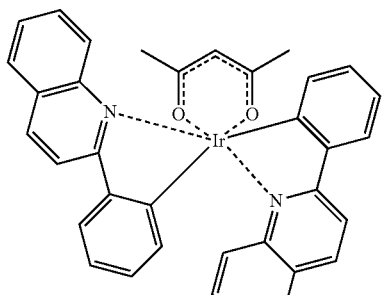

Ir(piq)₃

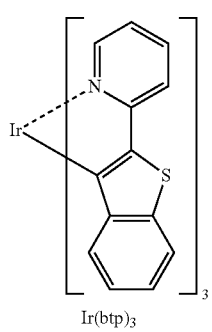

Ir(btp)₃

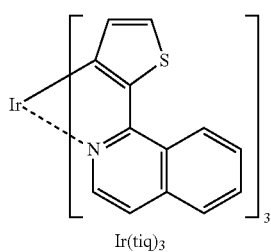

Ir(tiq)₃

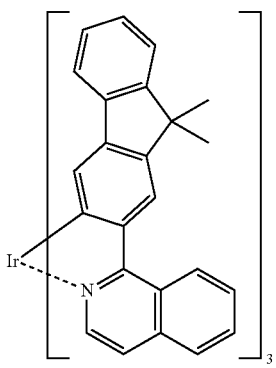

Ir(flil)₃

1. (Btp)₂Ir(III)(acac); Bis[2-(2'-benzothienyl)-pyridinato-N,C3']iridium (III)(acetylacetonate)
2. (Pq)₂Ir(III)(acac); Bis[(2-phenylquinolyl)-N,C2']iridium (III) (acetylacetonate)
3. (Piq)₂Ir(III)(acac); Bis[(1-phenylisoquinolinato-N,C2')]iridium (III) (acetylacetonate)
4. (DBQ)₂Ir(acac); Bis[(dibenzo[f,h]quinoxalino-N,C2')iridium (III)(acetylacetonate)
5. [Ir(HFP)₃], Tris(2,5-bis-2'-(9',9'-dihexylfluorene)pyridine)iridium (III)
6. Ir(piq)₃, Tris[1-phenylisoquinolinato-N,C2']iridium (III)
7. Ir(btp)₃, Tris-[2-(2'-benzothienyl)-pyridinato-N,C3']iridium (III)
8. Ir(tiq)₃, Tris[1-thiophen-2-ylisoquinolinato-N,C3']iridium (III)
9. Ir(fliq)₃; Tris[1-(9,9-dimethyl-9H-fluoren-2-yl)isoquinolinato-(N,C3')iridium (III))

A green light-emitting component may emit a combination of visible photons so that the light appears to have a green quality to an observer. In some embodiments, a green light-emitting component may emit visible photons having an average wavelength in the range of about 490 nm, about 500 nm, or about 501 nm to about 570 nm or about 600 nm. Some non-limiting examples of compounds which may form part or all of a green light-emitting component include iridium coordination compounds such as: Bis(2-phenylpyridinato-N,C2') iridium(III)(acetylacetonate) [Ir(ppy)₂(acac)], Bis(2-(4-tolyl)pyridinato-N,C2')iridium(III)(acetylacetonate) [Ir(mppy)₂(acac)], Bis(2-(4-tert-butyl)pyridinato-N,C2') iridium (III)(acetylacetonate) [Ir(t-Buppy)₂(acac)], Tris(2-phenylpyridinato-N,C2')iridium (III) [Ir(ppy)₃], Bis(2-phenyloxazolinato-N,C2')iridium (III) (acetylacetonate) [Ir(op)₂(acac)], Tris(2-(4-tolyl)pyridinato-N,C2')iridium(III) [Ir(mppy)₃], etc.

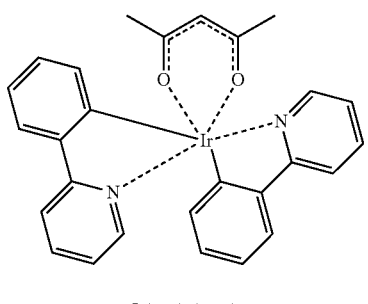

Ir(ppy)₂(acac)

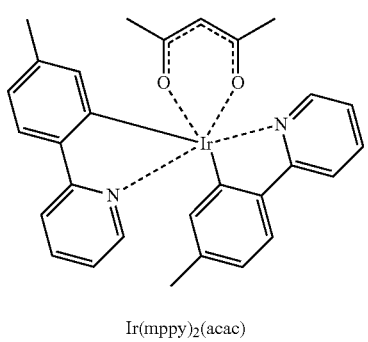

Ir(mppy)₂(acac)

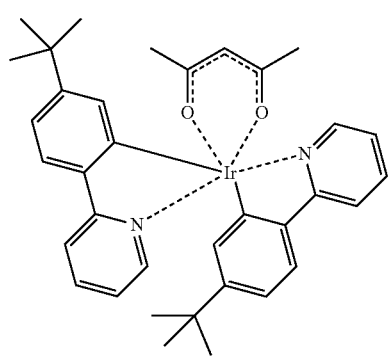

Ir(t-Buppy)₂(acac)

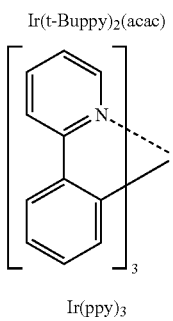

Ir(ppy)₃

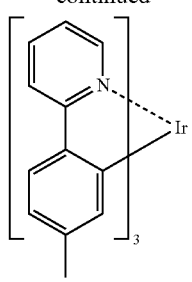

Ir(mppy)₃

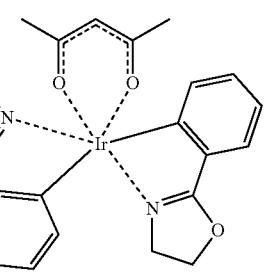

Ir(op)₂(acac)

An orange light-emitting component may emit a combination of visible photons so that the light appears to have an orange quality to an observer. In some embodiments, an orange light-emitting component may emit visible photons having an average wavelength in the range of about 570 nm, about 585 nm, or about 601 nm to about 620 nm or about 650 nm. Some non-limiting examples of compounds which may form part or all of an orange light-emitting component include iridium coordination compounds such as: Bis[2-phenylbenzothiazolato-N,C2']iridium (III)(acetylacetonate), Bis[2-(4-tert-butylphenyl)benzothiazolato-N,C2']iridium(III)(acetylacetonate), Bis[(2-(2'-thienyl)pyridinato-N,C3')]iridium (III) (acetylacetonate), Tris[2-(9,9-dimethylfluoren-2-yl)pyridinato-(N,C3')]iridium (III), Tris[2-(9,9-dimethylfluoren-2-yl)pyridinato-(N,C3')]iridium (III), Bis[5-trifluoromethyl-2-[3-(N-phenylcarbzolyl)pyridinato-N,C2']iridium(III)(acetylacetonate), (2-PhPyCz)₂Ir(III)(acac), etc.

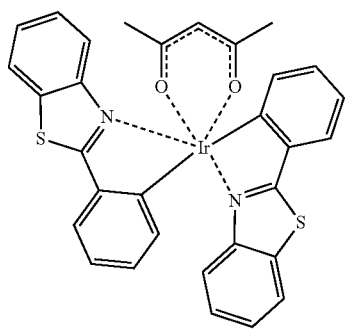

(bt)₂Ir(III)(acac)
Bis[2-phenylbenzothiazolato-N,C2']iridium (III)(acetylacetonate)

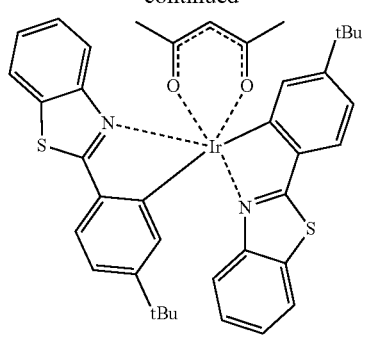

(t-bt)₂Ir(III)(acac)
Bis[2-(4-tert-butylphenyl)benzothiazolato-N,C2']iridium(III)(acetylacetonate)

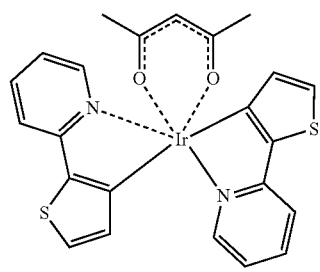

(thp)₂Ir(III)(acac)
Bis[(2-(2'-thienyl)pyridinato-N,C3')]iridium (III) (acetylacetonate)

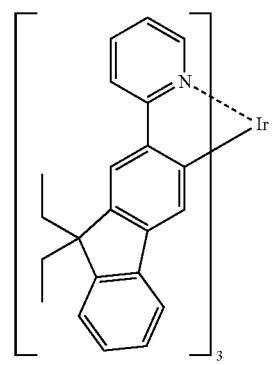

[Ir(Flpy)₃]
Tris[2-(9,9-dimethylfluoren-2-yl)pyridinato-(N,C3')]iridium (III)

-continued

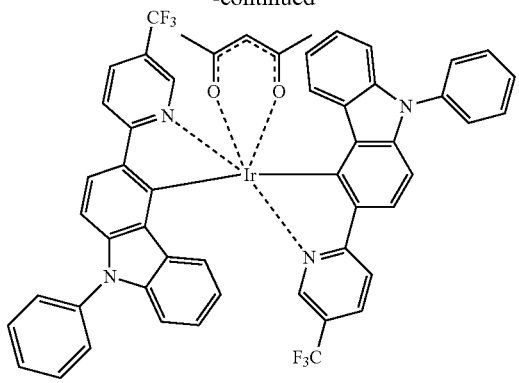

(Cz—CF₃)Ir(III)(acac)
Bis[5-trifluoromethyl-2-[3-(N-phenylcarbzolyl)pyridinato-N,C2']iridium(III)(acetylacetonate)

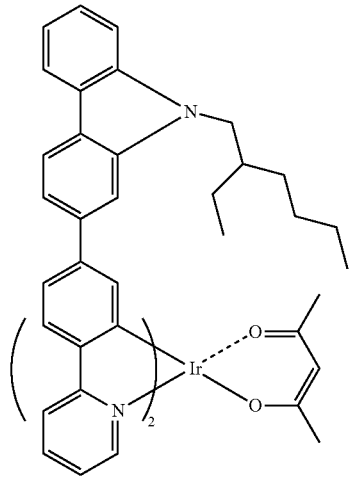

(2-PhPyCz)₂Ir(III)(acac)

The thickness of a light-emitting layer may vary. In one embodiment, a light-emitting layer may have a thickness in the range of from about 1 nm to about 150 nm or about 200 nm.

In some embodiments, the light-emitting device may emit white light. A light-emitting layer may be configured to emit white light by including a white light emitter, or a combination of colored emitters which have a combined emission that appears white. Alternatively, a combination of different colored light-emitting layers may be configured to emit white light.

In some embodiments, the organic component may further comprise a hole-transport layer disposed between the anode and the light-emitting layer. The hole-transport layer may comprise at least one hole-transport material. In some embodiments, the hole-transport material comprises at least one of an aromatic-substituted amine, a carbazole, a polyvinylcarbazole (PVK), e.g. poly(9-vinylcarbazole); polyfluorene; a polyfluorene copolymer; poly(9,9-di-n-octylfluorene-alt-benzothiadiazole); poly(paraphenylene); poly[2-(5-cyano-5-methylhexyloxy)-1,4-phenylene]; a benzidine; a phenylenediamine; a phthalocyanine metal complex; a polyacetylene; a polythiophene; a triphenylamine; copper phthalocyanine; 1,1-Bis(4-bis(4-methylphenyl)aminophenyl)cyclohexane; 2,9-Dimethyl-4,7-diphenyl-1,10-phenanthroline; 3,5-Bis(4-tert-butyl-phenyl)-4-phenyl[1,2,4]triazole; 3,4,5-Triphenyl-1,2,3-triazole; 4,4',4'-tris(3-methylphenylphenylamino)triphenylamine (MTDATA); N,N'-bis(3-methylphenyl)N,N'-diphenyl-[1,1'-biphenyl]-4,4'-diamine (TPD); 4,4'-bis[N-(naphthyl)-N-phenyl-amino]biphenyl (α-NPB); 4,4',4"-tris(carbazol-9-yl)-triphenylamine (TCTA); 4,4'-bis[N,N'-(3-tolyl)amino]-3,3'-dimethylbiphenyl (HMTPD); 4,4'-N,N'-dicarbazole-biphenyl (CBP); 1,3-N,N-dicarbazole-benzene (mCP); Bis[4-(p,p'-ditolyl-amino)phenyl] diphenylsilane (DTASi); 2,2'-bis(4-carbazolylphenyl)-1,1'-biphenyl (4CzPBP); N,N'N"-1,3,5-tricarbazoloylbenzene (tCP); N,N'-bis(4-butylphenyl)-N,N'-bis(phenyl)benzidine; or the like.

In some embodiments, the organic component may further comprise an electron-transport layer disposed between the cathode and the light-emitting layer. In some embodiments, the electron-transport layer may comprise a compound described herein. Other electron-transport materials may be included, such as 2-(4-biphenylyl)-5-(4-tert-butylphenyl)-1,3,4-oxadiazole (PBD); 1,3-bis(N,N-t-butyl-phenyl)-1,3,4-oxadiazole (OXD-7), 1,3-bis[2-(2,2'-bipyridine-6-yl)-1,3,4-oxadiazo-5-yl]benzene; 3-phenyl-4-(1'-naphthyl)-5-phenyl-1,2,4-triazole (TAZ); 2,9-dimethyl-4,7-diphenyl-phenanthroline (bathocuproine or BCP); aluminum tris(8-hydroxyquinolate) (Alq3); and 1,3,5-tris(2-N-phenylbenzimidazolyl)benzene; 1,3-bis[2-(2,2'-bipyridine-6-yl)-1,3,4-oxadiazo-5-yl]benzene (BPY-OXD); 3-phenyl-4-(1'-naphthyl)-5-phenyl-1,2,4-triazole (TAZ), 2,9-dimethyl-4,7-diphenyl-phenanthroline (bathocuproine or BCP); and 1,3,5-tris[2-N-phenylbenzimidazol-z-yl]benzene (TPBI). In some embodiments, the electron transport layer may be aluminum quinolate (Alq₃), 2-(4-biphenylyl)-5-(4-tert-butylphenyl)-1,3,4-oxadiazole (PBD), phenanthroline, quinoxaline, 1,3,5-tris[N-phenylbenzimidazol-z-yl]benzene (TPBI), or a derivative or a combination thereof.

If desired, additional layers may be included in the light-emitting device. These additional layers may include an electron injection layer (EIL), a hole-blocking layer (HBL), an exciton-blocking layer (EBL), and/or a hole-injection layer (HIL). In addition to separate layers, some of these materials may be combined into a single layer.

In some embodiments, the light-emitting device can include an electron injection layer between the cathode layer and the light emitting layer. In some embodiments, the lowest unoccupied molecular orbital (LUMO) energy level of the electron injection material(s) is high enough to prevent it from receiving an electron from the light emitting layer. In other embodiments, the energy difference between the LUMO of the electron injection material(s) and the work function of the cathode layer is small enough to allow the electron injection layer to efficiently inject electrons into the light-emitting layer from the cathode. A number of suitable electron injection materials are known to those skilled in the art. Examples of suitable electron injection material(s) include but are not limited to, an optionally substituted compound selected from the following: LiF, CsF, Cs doped into electron transport material as described above or a derivative or a combination thereof.

In some embodiments, the device can include a hole-blocking layer, e.g., between the cathode and the light-emitting layer. Various suitable hole-blocking materials that can be included in the hole-blocking layer are known to those skilled in the art. Suitable hole-blocking material(s) include but are not limited to, an optionally substituted compound selected from the following: bathocuproine (BCP), 3,4,5-triphenyl-1,2,4-triazole, 3,5-bis(4-tert-butyl-phenyl)-4-phenyl-[1,2,4]

triazole, 2,9-dimethyl-4,7-diphenyl-1,10-phenanthroline, and 1,1-bis(4-bis(4-methylphenyl)aminophenyl)-cyclohexane.

In some embodiments, the light-emitting device can include an exciton-blocking layer, e.g., between the light-emitting layer and the anode. In an embodiment, the band gap energy of the material(s) that comprise exciton-blocking layer may be large enough to substantially prevent the diffusion of excitons. A number of suitable exciton-blocking materials that can be included in the exciton-blocking layer are known to those skilled in the art. Examples of material(s) that can compose an exciton-blocking layer include an optionally substituted compound selected from the following: aluminum quinolate ($Alq_3$), 4,4'-bis[N-(naphthyl)-N-phenyl-amino]biphenyl (α-NPB), 4,4'-N,N'-dicarbazole-biphenyl (CBP), and bathocuproine (BCP), and any other material(s) that have a large enough band gap to substantially prevent the diffusion of excitons.

In some embodiments, the light-emitting device can include a hole-injection layer between the light-emitting layer and the anode. Various suitable hole-injection materials that can be included in the hole-injection layer are known to those skilled in the art. Exemplary hole-injection material(s) include an optionally substituted compound selected from the following: a polythiophene derivative such as poly(3,4-ethylenedioxythiophene (PEDOT)/polystyrene sulphonic acid (PSS), a benzidine derivative such as N,N,N',N'-tetraphenylbenzidine, poly(N,N'-bis(4-butylphenyl)-N,N'-bis(phenyl) benzidine), a triphenylamine or phenylenediamine derivative such as N,N'-bis(4-methylphenyl)-N,N'-bis(phenyl)-1,4-phenylenediamine, 4,4',4"-tris(N-(naphthylen-2-yl)-N-phenylamino)triphenylamine, an oxadiazole derivative such as 1,3-bis(5-(4-diphenylamino)phenyl-1,3,4-oxadiazol-2-yl) benzene, a polyacetylene derivative such as poly(1,2-bis-benzylthio-acetylene), and a phthalocyanine metal complex derivative such as phthalocyanine copper (CuPc). In some embodiments, hole-injection materials, while still being able to transport holes, may have a hole mobility substantially less than the hole mobility of conventional hole transport materials.

Light-emitting devices comprising the compounds described herein can be fabricated using techniques known in the art, as informed by the guidance provided herein. For example, a glass substrate can be coated with a high work functioning metal such as ITO which can act as an anode. After patterning the anode layer, a hole-injection and/or hole-transport layer may be deposited on the anode in that order. A light-emitting layer that includes a light-emitting component can be deposited on the anode, the hole-transport layer, or the hole-injection layer. The light-emitting layer may contain a compound described herein, and/or a compound described herein may be part of an electron-transport layer and/or an electron-injecting layer, deposited in that order, or may be part of an electron-injecting and electron-transport layer. The cathode layer, comprising a low work functioning metal (e.g., Mg:Ag), can then be deposited, e.g., by vapor deposition or sputtering. The device may also contain an exciton-blocking layer, an electron blocking layer, a hole blocking layer, a second light-emitting layer, or other layers that can be added to the device using suitable techniques.

An example of a configuration of the device comprising a compound described herein is shown in FIG. 1. The device comprises the following layers in the order given: an ITO/Glass anode 5, a PEDOT/PSS hole-injection layer 10, a hole-transport layer (NPB) 15, a light-emitting layer 20, an electron-transport layer (TPBI) 30, and a LiF/Al cathode 35.

In some embodiments, the OLED may be made by a wet process such as a process that comprises at least one of spraying, spin coating, drop casting, inkjet printing, screen printing, etc. Some embodiments provide a composition which may be a liquid suitable for deposition onto a substrate. The liquid may be a single phase, or may comprise one or more additional solid or liquid phases dispersed in it. The liquid typically comprises a light-emitting compound, a host material described herein and a solvent.

The following are examples of some methods that may be used to prepare compounds described herein.

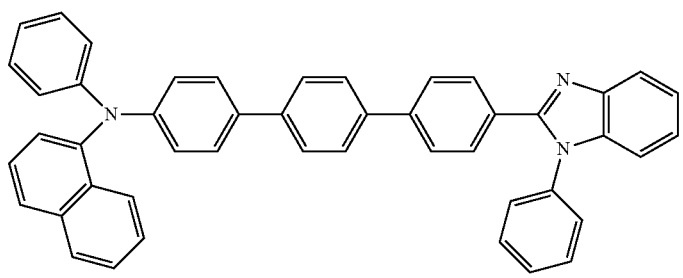

Host-1

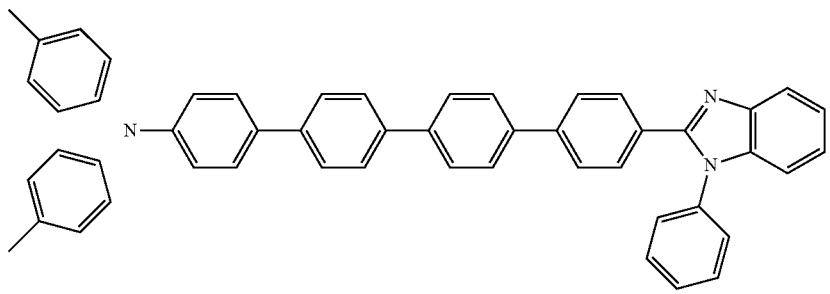

Host-3

Host-2
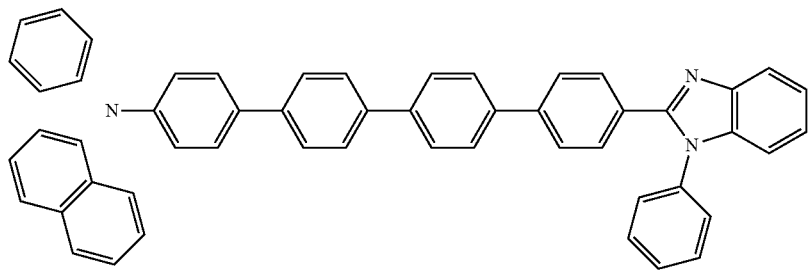
Host-4
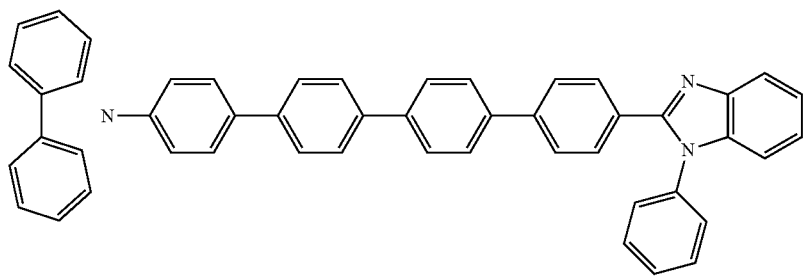
Example 1
Organic Synthesis
Example 1.1
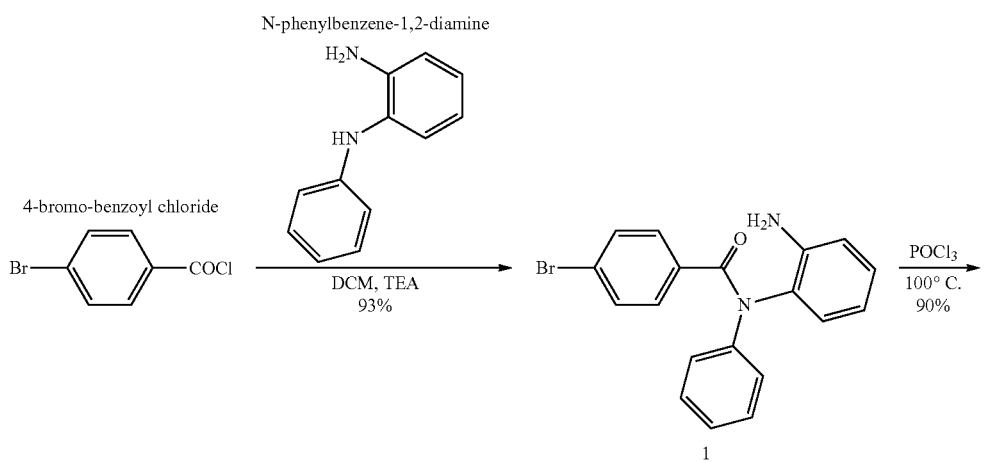

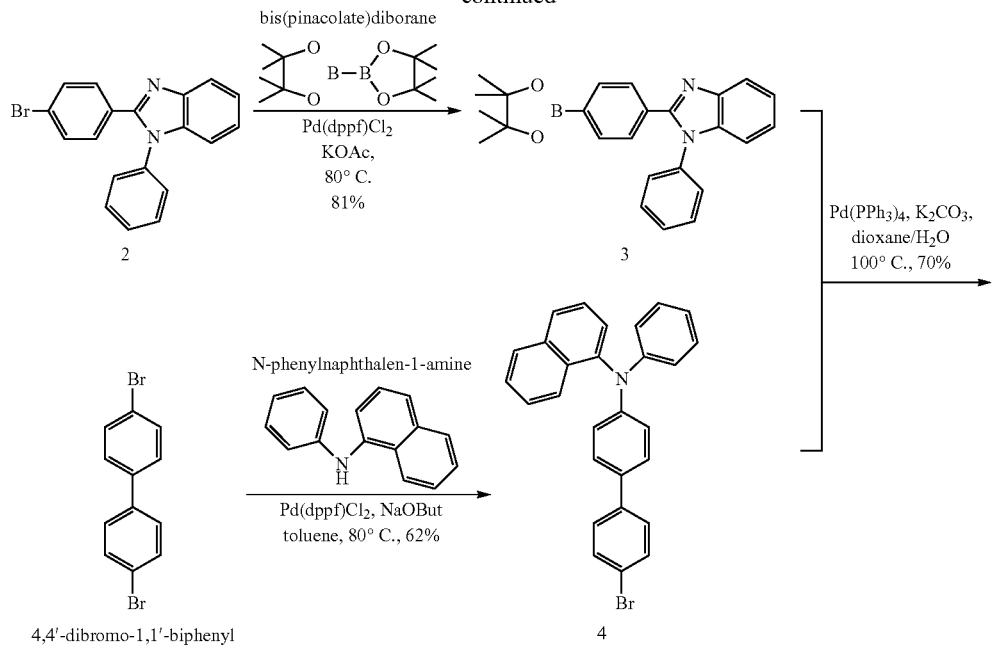

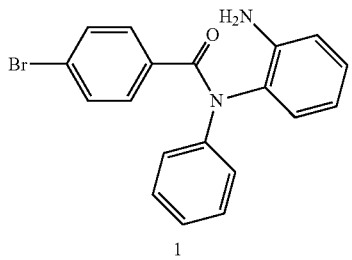

Host-1

Example 1.1.1

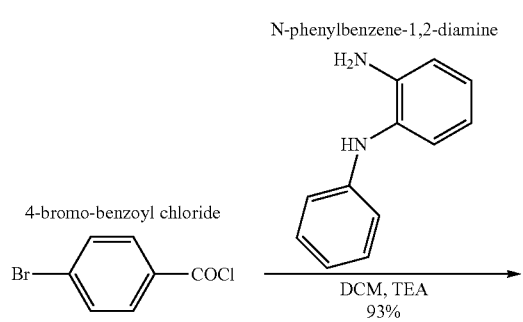

4-Bromo-N-(2-(phenylamino)phenyl)benzamide (1): To a solution of 4-bromo-benzoyl chloride (11 g, 50 mmol) in anhydrous dichloromethane (DCM) (100 ml), was added N-phenylbenzene-1,2-diamine (10.2 g, 55 mmol), then triethylamine (TEA) (17 ml, 122 mmol) slowly. The whole was stirred at room temperature (RT) overnight. Filtration gave a white solid 1 (6.5 g). The filtrate was worked up with water (300 ml), then extracted with DCM (300 ml) three times. The organic phase was collected and dried over MgSO$_4$, concentrated and recrystallized in DCM/hexanes to give another portion of white solid 1 (10.6 g). Total amount of product 1 is 17.1 g, in 93% yield.

Example 1.1.2

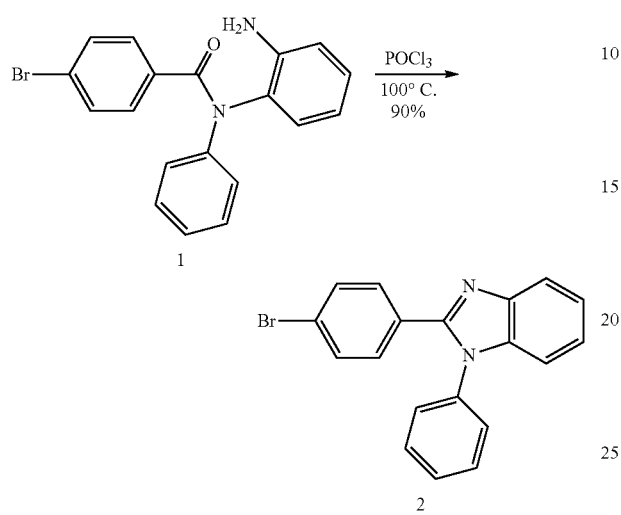

2-(4-bromophenyl)-1-phenyl-1H-benzo[d]imidazole (2): To a suspension of amide 1 (9.6 g, 26 mmol) in anhydrous 1,4-dioxane (100 mL) was added phosphorus oxychloride (POCl$_3$) (9.2 mL, 100 mmol) slowly. The whole was then heated at 100° C. overnight. After cooling to RT, the mixture was poured into ice (200 g) with stirring. Filtration, followed by recrystallization in DCM/hexanes gave a pale grey solid 2 (8.2 g, in 90% yield).

Example 1.1.3

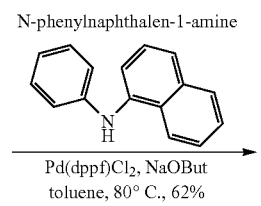

1-phenyl-2-(4-(4,4,5,5-tetramethyl-1,3,2-dioxaborolan-2-yl)phenyl)-1H-benzo[d]imidazole (3): A mixture of Compound 2 (0.70 g, 2 mmol), bis(pinacolate)diborane (0.533 g, 2.1 mmol), bis(diphenylphosphino)ferrocene]dichloropalladium (Pd(dppf)Cl$_2$) (0.060 g, 0.08 mmol) and anhydrous potassium acetate (KOAc) (0.393 g, 4 mmol) in 1,4-dioxane (20 ml) was heated at 80° C. under argon overnight. After cooling to RT, the whole was diluted with ethyl acetate (80 ml) then filtered. The solution was absorbed on silica gel, then purified by column chromatography (hexanes/ethyl acetate 5:1 to 3:1) to give a white solid 3 (0.64 g, in 81% yield).

Example 1.1.4

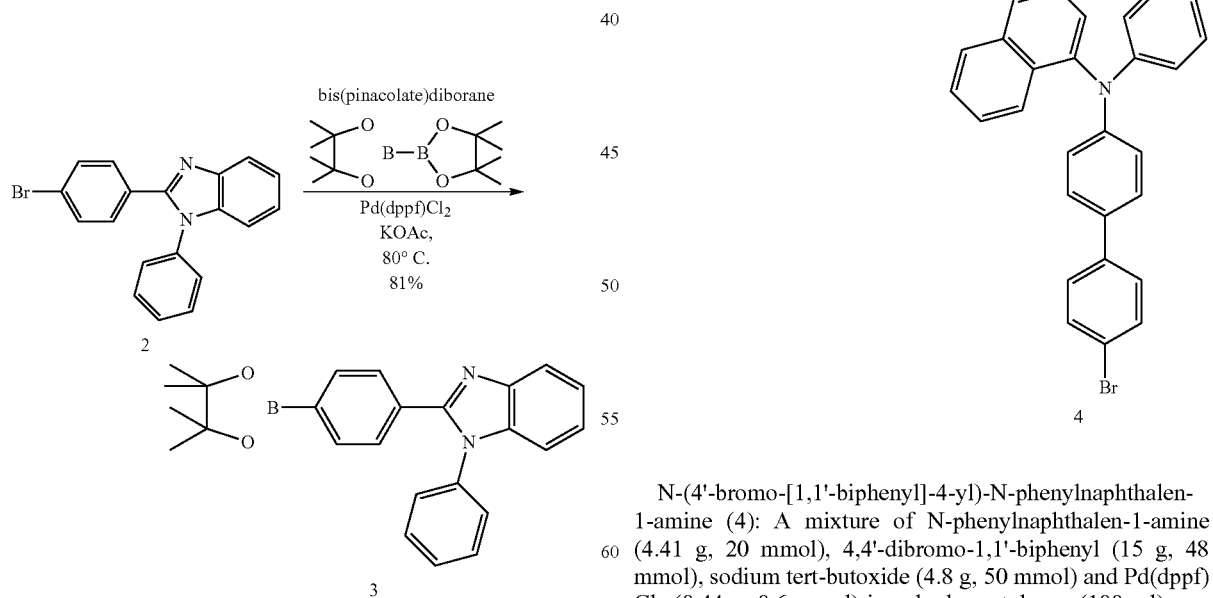

N-(4'-bromo-[1,1'-biphenyl]-4-yl)-N-phenylnaphthalen-1-amine (4): A mixture of N-phenylnaphthalen-1-amine (4.41 g, 20 mmol), 4,4'-dibromo-1,1'-biphenyl (15 g, 48 mmol), sodium tert-butoxide (4.8 g, 50 mmol) and Pd(dppf)Cl$_2$ (0.44 g, 0.6 mmol) in anhydrous toluene (100 ml) was degassed and heated at 80° C. for 10 hours. After cooling to RT, the mixture was poured into dichloromethane (400 ml) and stirred for 30 min, then washed with brine (100 ml). The organic is collected and dried over Na$_2$SO$_4$, loaded on silica gel, and purified by flash column (hexanes to hexanes/ethyl acetate 90:1) to give a solid which was washed with methanol and dried under air to give a white solid 4 (5.58 g, in 62% yield).

Example 1.1.5

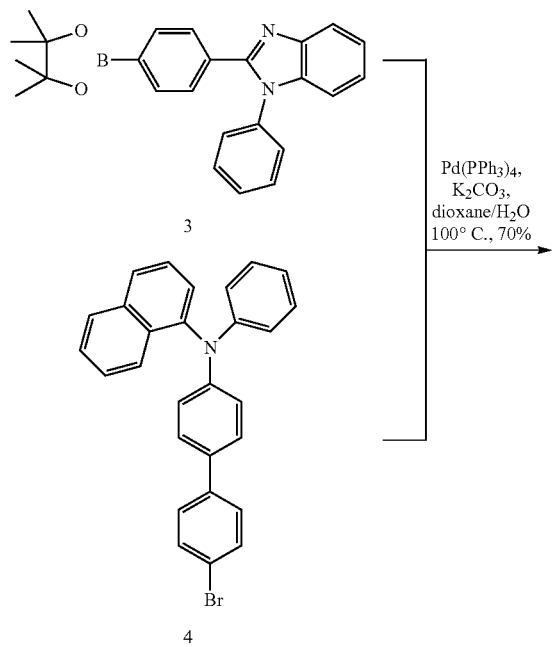

Example 1.2

1) (0.90 g, in 70% yield). LCMS data: calcd for $C_{47}H_{34}N_3$ (M+H)=640.3. found: m/e=640.

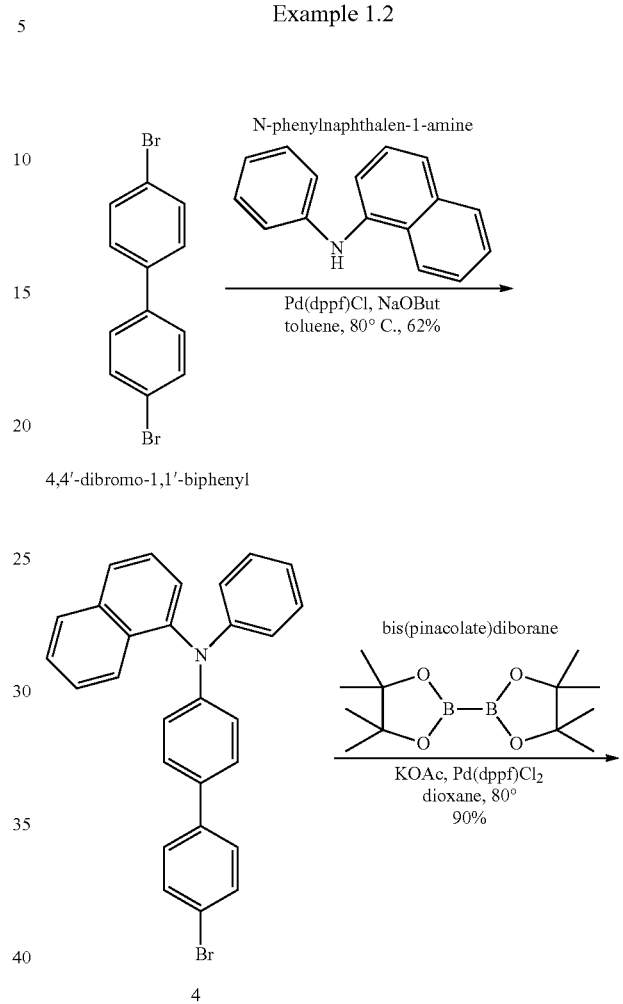

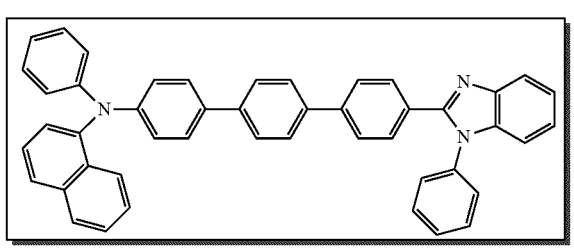

Host-1

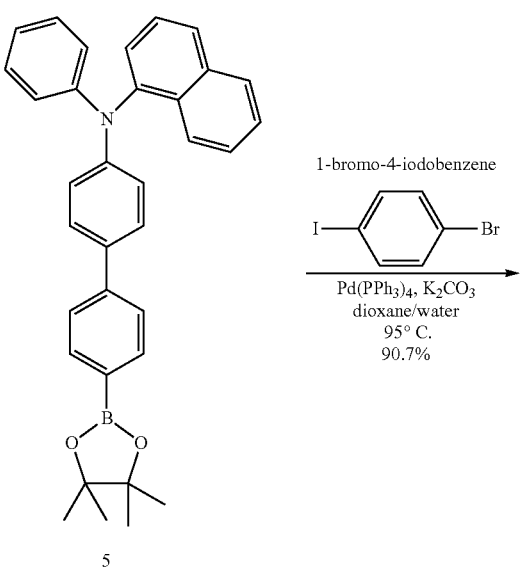

Host-1: A mixture of Compound 3 (0.80 g, 2 mmol), Compound 4 (0.90, 2 mmol), tetrakis(triphenylphosphine)palladium(0) (Pd(PPh$_3$)$_4$) (0.115 g, 0.1 mmol) and potassium carbonate (0.69 g, 5 mmol) in dioxane/water (25 ml/5 ml) was degassed and heated at 100° C. overnight. After cooling down to RT, the mixture was worked up with water and ethyl acetate (150 ml×3). The organic phase is collected and dried over Na$_2$SO$_4$, loaded on silica gel, purified by flash column (hexanes/ethyl acetate 8:1 to 6:1) to give an off white solid (Host-

Example 1.2.1

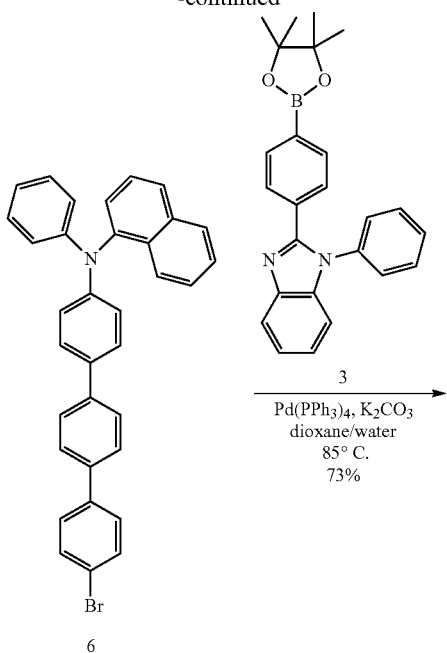

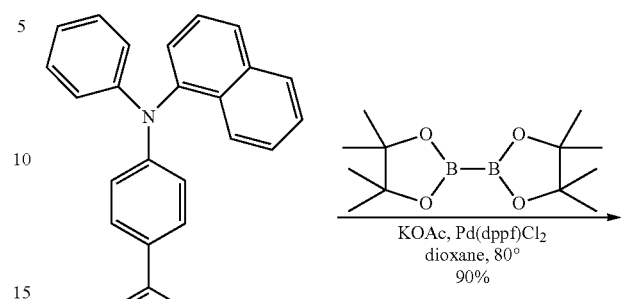

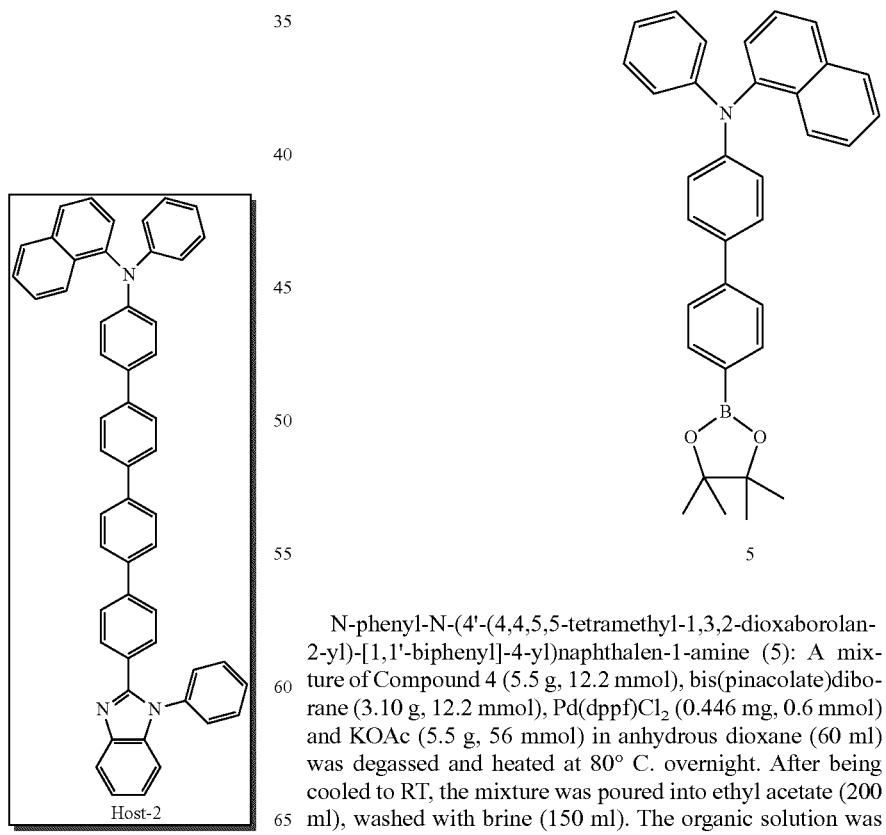

N-phenyl-N-(4'-(4,4,5,5-tetramethyl-1,3,2-dioxaborolan-2-yl)-[1,1'-biphenyl]-4-yl)naphthalen-1-amine (5): A mixture of Compound 4 (5.5 g, 12.2 mmol), bis(pinacolate)diborane (3.10 g, 12.2 mmol), Pd(dppf)Cl$_2$ (0.446 mg, 0.6 mmol) and KOAc (5.5 g, 56 mmol) in anhydrous dioxane (60 ml) was degassed and heated at 80° C. overnight. After being cooled to RT, the mixture was poured into ethyl acetate (200 ml), washed with brine (150 ml). The organic solution was dried over Na$_2$SO$_4$, loaded on silica gel and purified by flash column (hexanes to hexanes/ethyl acetate 30:1) to collect the major fraction. After removal of solvent, the solid was washed with methanol, filtered and dried in air to give a white solid 5 (5.50 g, in 90% yield).

Example 1.2.2

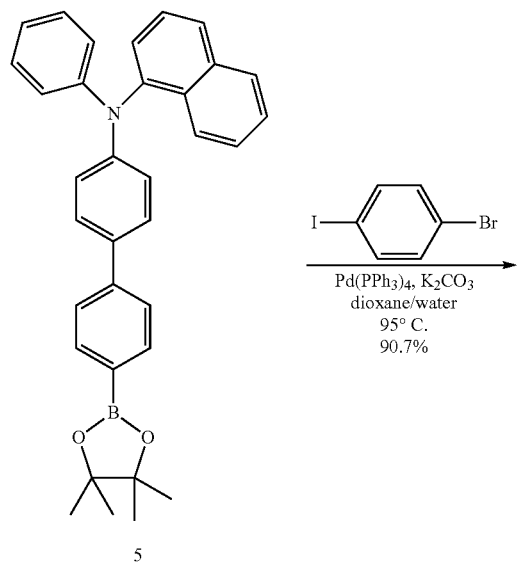

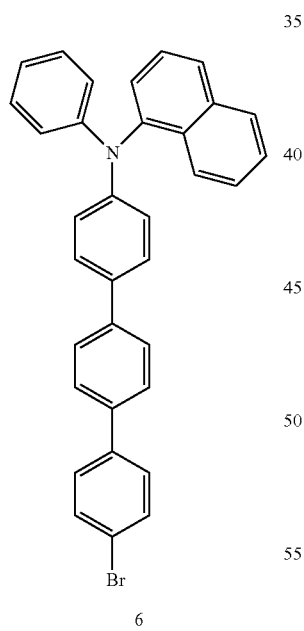

N-(4"-bromo-[1,1':4',1"-terphenyl]-4-yl)-N-phenylnaphthalen-1-amine (6): A mixture of Compound 5 (4.5 g, 9.0 mmol), 1-bromo-4-iodobenzene (5.12 g, 18 mmol), Pd(PPh$_3$)$_4$ (0.52 g, 0.45 mmol) and potassium carbonate (4.436 g, 32 mmol) in dioxane/water (150 ml/30 ml) was degassed and heated at 95° C. overnight. After being cooled to RT, the mixture was poured into dichloromethane (300 ml), washed with brine, dried over Na$_2$SO$_4$, then loaded on silica gel, purified by flash column (hexanes to hexanes/ethyl acetate 20:1) to give a light yellow solid (4.30 g, in 90.7% yield).

Example 1.2.3

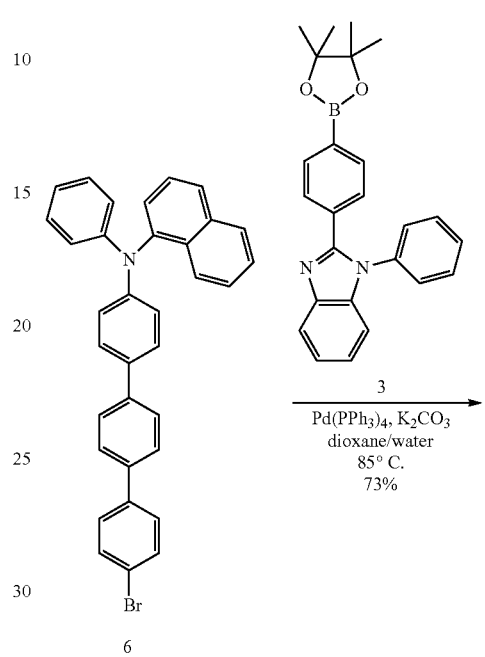

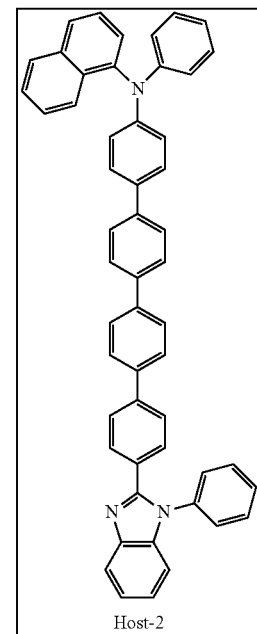

Host-2: A mixture of Compound 6 (4.21 g, 8.0 mmol), compound 3 (3.166 g, 8.0 mmol), Pd(PPh$_3$)$_4$ and potassium carbonate (3.31 g, 24 mmol) in dioxane/water (150 ml/30 ml) was degassed and heated at 85° C. for 18 hours. After being cooled to RT, the mixture was filtered. The solid and the filtrate were collected separately. The filtrate was diluted with dichoromethane (250 ml) and washed with brine. The organic phase was dried over Na$_2$SO$_4$, loaded on silica gel and purified by flash column (hexanes to hexanes/ethyl acetate 10:1 to 5:1 to 4:1). The major desired blue fluorescent fraction was collected, and concentrated to give a white solid (0.55 g, with m/e=716 corresponding to the target molecular weight). The solid from the first filtration was redissolved in dichloromethane (200 ml), loaded on silica gel, and purified by flash column (hexanes to hexanes/ethyl acetate 4:1 to dichloromethane to hexanes/ethyl acetate 3:1) to collect the desired fraction, concentrated to 200 ml and kept in −10 C overnight. The white precipitate was filtered and dried in air to give a floppy white solid, Host-2 (3.65 g). The overall yield is 73%. LCMS data: calcd for $C_{53}H_{38}N_3$ (M+H): 716.3. found m/e=716.

Example 1.3

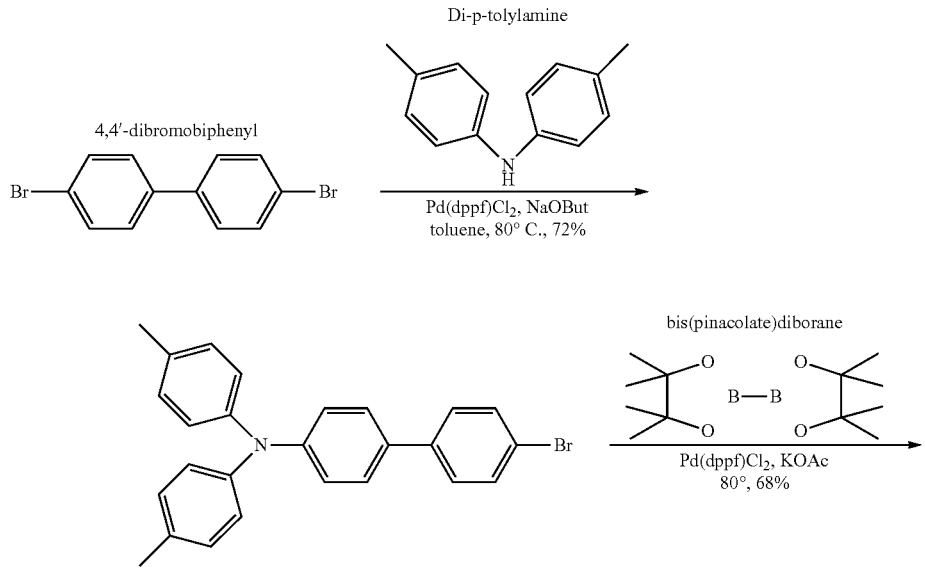

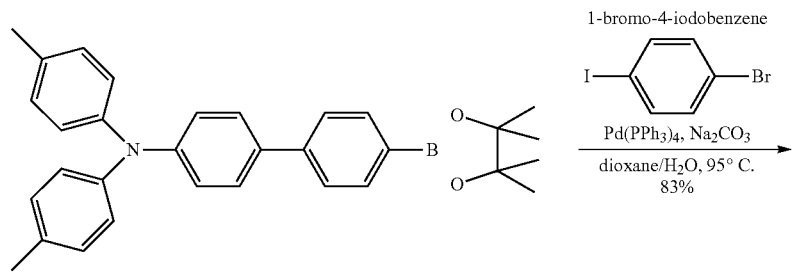

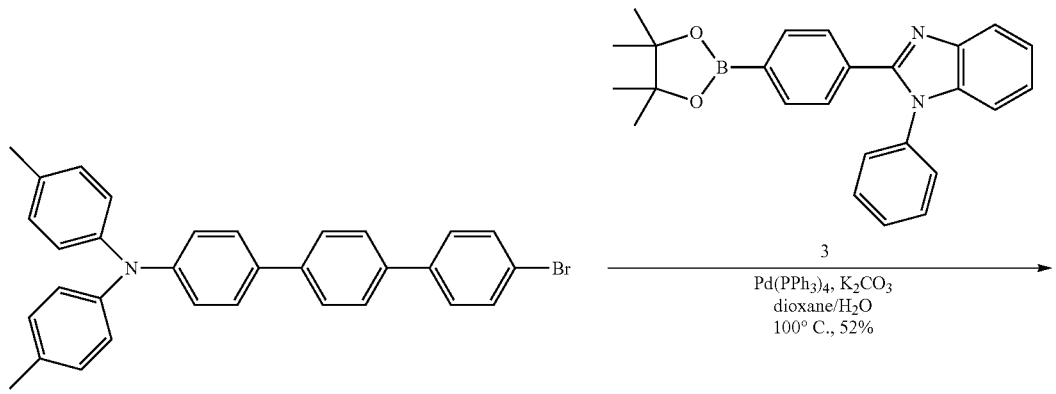

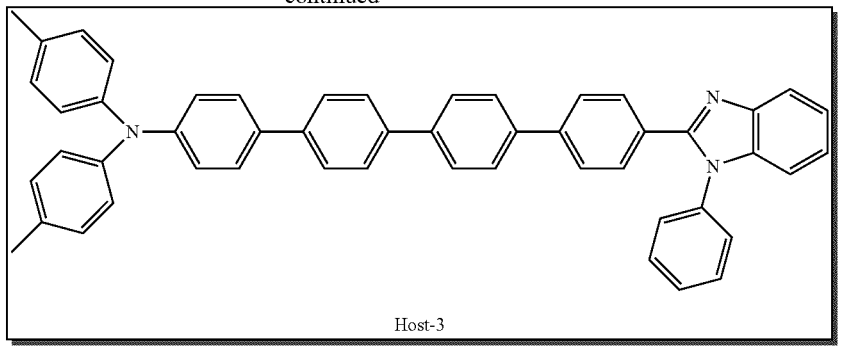

Host-3

Example 1.3.1

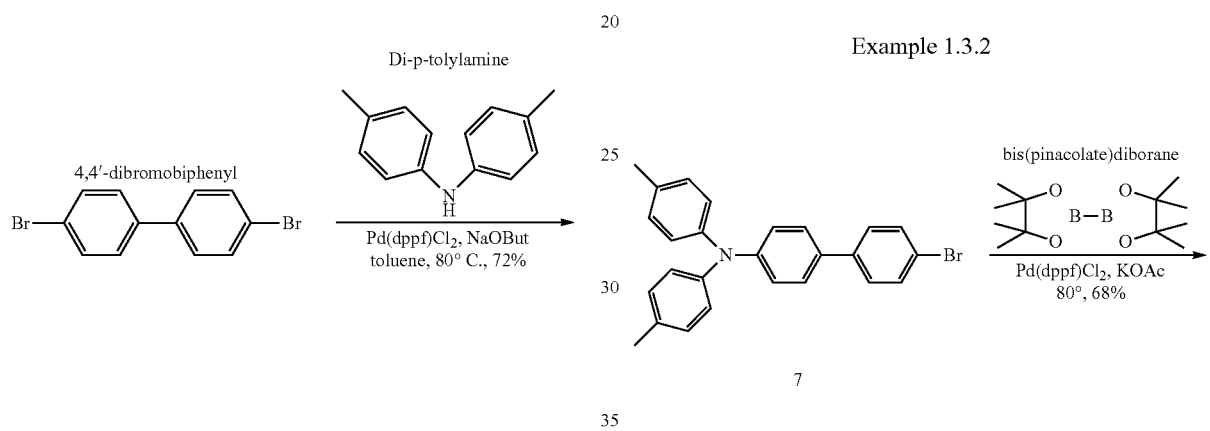

4'-bromo-N,N-dip-tolylbiphenyl-4-amine (7): Di-p-tolylamine (6.0 g, 30.4 mmol), 4,4'-dibromobiphenyl (23.7 g, 76.0 mmol), sodium tert-butoxide (7.26 g, 91.2 mmol), and [1,1-bis(diphenylphosphino)ferrocene]palladium(II) dichloride (Pd(dppf)Cl$_2$) (666 mg, 0.912 mmol, 3 mol %) were added to anhydrous toluene (about 250 ml) and degassed in argon for about 30 minutes. The resulting mixture was heated to about 80° C. for about 6 hours, after which a TLC analysis indicated that most of the di-p-tolylamine was consumed. After being cooled to RT, the mixture was poured into saturated aqueous sodium bicarbonate and extracted with 2 portions of ethyl acetate. The organic layers were pooled and washed with water and brine, then dried over MgSO$_4$. After filtration the extract was concentrated to dryness on a rotary evaporator, then loaded onto silica gel. A flash column (gradient of 100% hexane to 1% methylene chloride in hexane) resulted in 9.4 g (72%) of a white solid Compound 7 confirmed by $^1$H NMR in CDCl$_3$.

Example 1.3.2

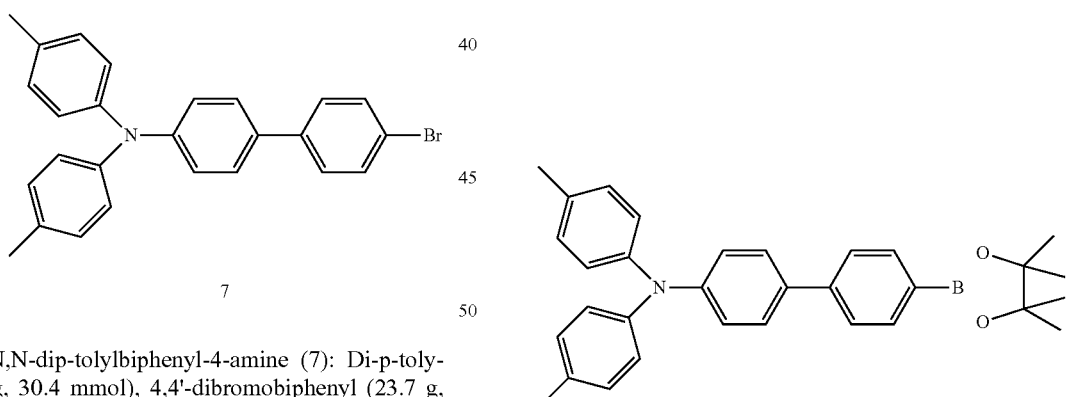

4'-(4,4,5,5-tetramethyl-1,3,2-dioxaborolan-2-yl)-N,N-di-p-tolyl-[1,1'-biphenyl]-4-amine (8): A mixture of Compound 7 (2.0 g, 4.67 mmol), bis(pinacolate)diborane (1.27 g, 5 mmol), Pd(dppf)Cl$_2$ (0.18 g, 0.25 mmol) and potassium acetate (0.98 g, 10 mmol) in anhydrous dioxane (50 ml) was degassed and heated at 80° C. for 16 hours. After being cooled to RT, the whole was poured into ethyl acetate (100 ml) and filtered off solid. The organic solution was loaded on silica gel, and purified by flash column (hexanes/ethyl acetate 6:1) to give a white solid 8 (1.5 g, in 68% yield).

Example 1.3.3

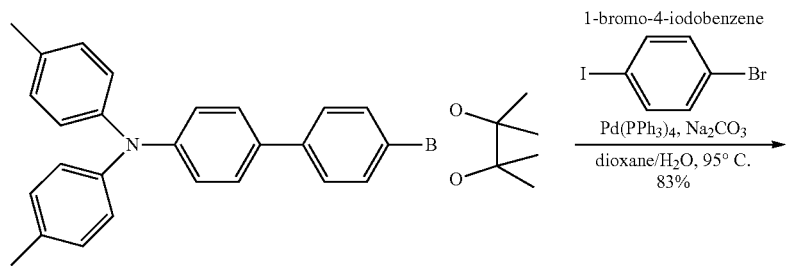

8

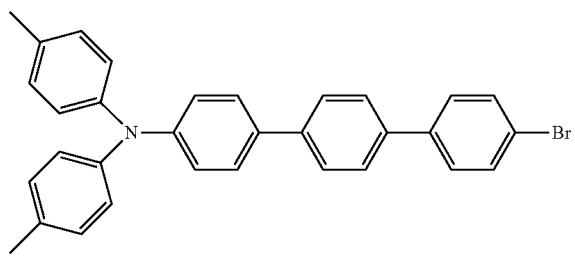

9

4"-bromo-N,N-di-p-tolyl-[1,1':4',1"-terphenyl]-4-amine (9): A mixture of compound 8 (3.0 g, 6.3 mmol), 1-bromo-4-iodobenzene (3.57 g, 12.6 mmol), Pd(PPh$_3$)$_4$ and potassium carbonate (1.74 g, 12.6 mmol) in dioxane/water (40 ml/8 ml) was degassed and heated at 95° C. for 24 hours. After being cooled to RT, yellow solid precipitated and collected by filtration. The solid was recrystallized in dichloromethane/methanol to give a pale yellow solid (2.22 g). The filtrate was loaded on silica gel and purified by flash column to give additional amount of yellow solid 9 (0.42 g). Total amount is 2.64 g, in 83% yield.

Example 1.3.4

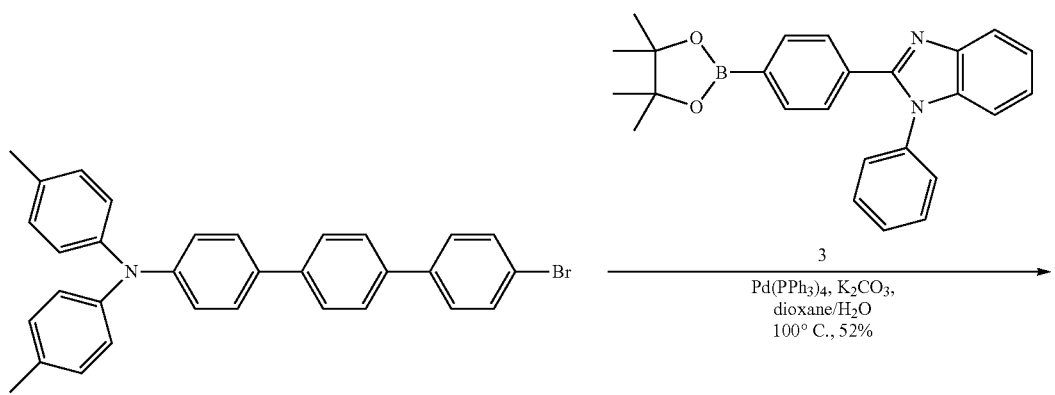

9

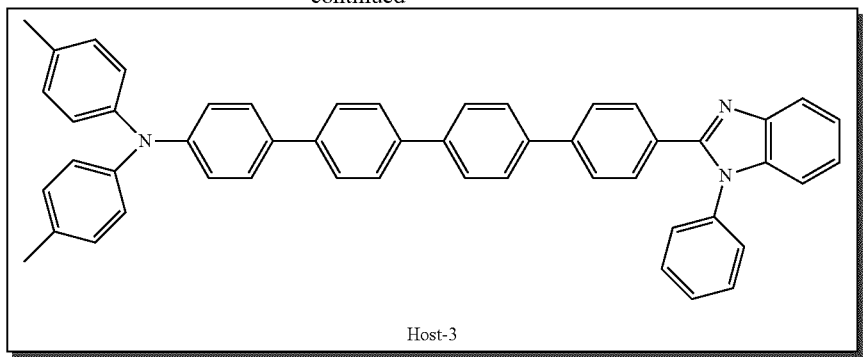

Host-3: A mixture of Compound 9 (1.50 g, 3 mmol), Compound 3 (1.18 g, 3 mmol), Pd(PPh$_3$)$_4$ (0.173 g, 0.15 mmol) and potassium carbonate (1.38 g, 10 mmol) in dioxane/water (40 ml/11 ml) was degassed and heated at 100° C. overnight. After being cooled to RT, the mixture was poured into dichloromethane (200 ml) then washed with water (150 ml×2). The organic solution was dried over Na$_2$SO$_4$, loaded on silica gel and purified by flash column (hexanes/dichloromethane 2:1 to hexanes/ethyl acetate 9:1 to 5:1) to give a white solid Host-3 (1.1 g, in 52% yield). LCMS data: calcd for C$_{51}$H$_4$ON$_3$ (M+H)=694.3. found m/e=694.

Example 1.4

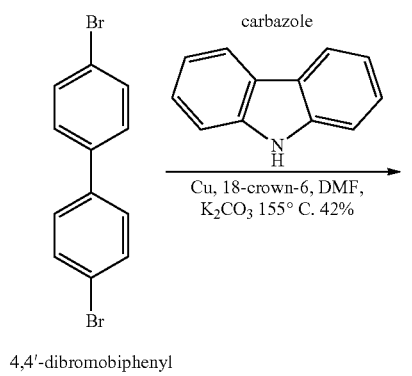

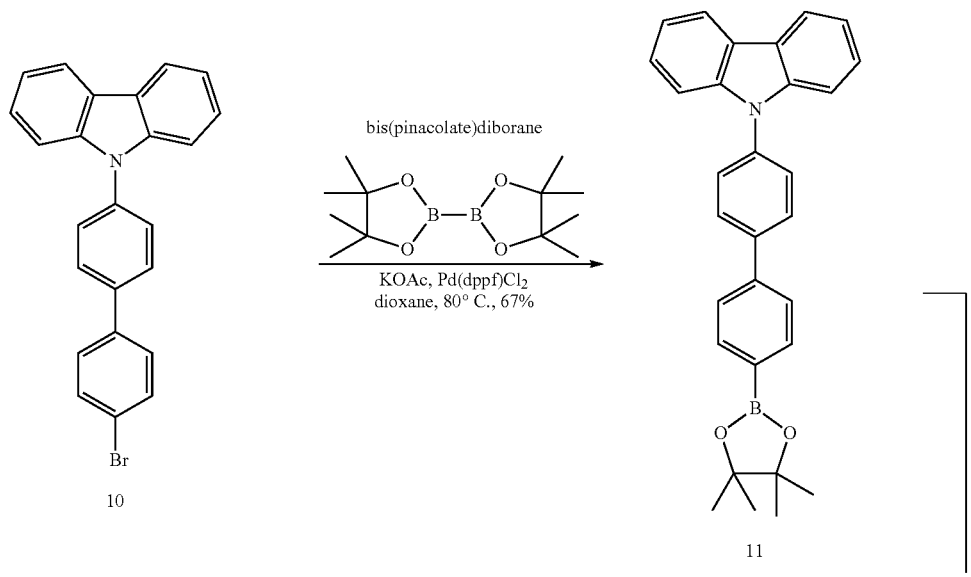

-continued
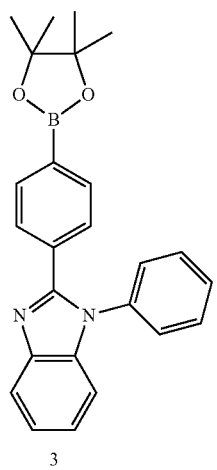
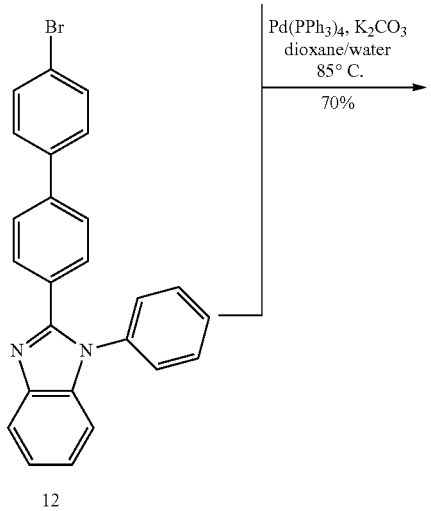
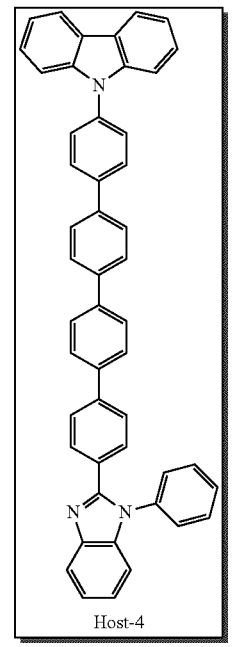
Example 1.4.1
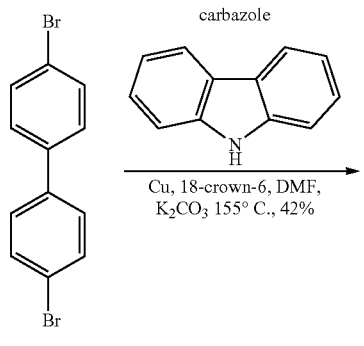
-continued
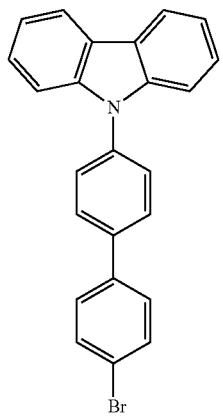

9-(4'-bromobiphenyl-4-yl)-9H-carbazole (10): A mixture of carbazole (300 mg, 1.81 mmol), 4,4'-dibromobiphenyl (846 mg, 2.71 mmol), copper (344 mg, 5.43 mmol), 18-crown-6 (187 mg, 0.71 mmol), potassium carbonate (750 mg, 5.43 mmol), and anhydrous N, N-dimethylformamide (10 ml) was degassed for 30 minutes. The mixture was heated at about 155° C. for 66 hours under argon. After being cooled to RT, the mixture was poured into methylene chloride (400 ml) and the subsequent mixture was filtered. The filtrate was loaded on silica gel. A flash column (silica, 10% methylene chloride in hexane) and reprecipitation in methylene chloride/hexanes yielded 304 mg (42% yield) of pure product 10; confirmed by HNMR.

Example 1.4.2

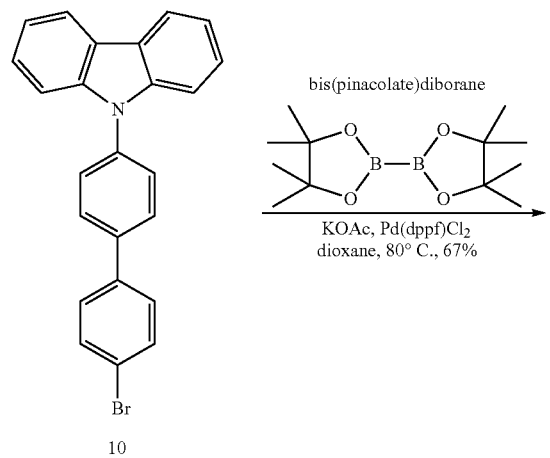

column (hexanes to hexanes/dichloromethane 5:1 to hexanes/ethyl acetate 8:1) to afford a white solid 11 (1.50 g, in 67% yield).

Example 1.4.3

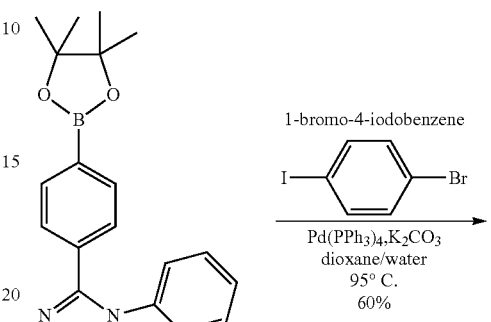

9-(4'-(4,4,5,5-tetramethyl-1,3,2-dioxaborolan-2-yl)-[1,1'-biphenyl]-4-yl)-9H-carbazole (11): A mixture of compound 10 (2.0 g, 5.02 mmol), bis(pinacolate)diborane (1.276 g, 5.02 mmol), Pd(dppf)Cl₂ (150 mg, 0.20 mmol) and potassium acetate (4.0 g, 41 mmol) in anhydrous dioxane (50 ml) was degassed and heated at 80° C. overnight. After being cooled to RT, the mixture was poured into brine, and extracted with ethyl acetate (200 ml). The organic phase was collected and dried over Na₂SO₄, then loaded on silica gel, purified by flash 2-(4'-bromo-[1,1'-biphenyl]-4-yl)-1-phenyl-1H-benzo[d]imidazole (12): A mixture of compound 3 (4.01 g, 10.1 mmol), 1-bromo-4-iodobenzene (5.73 g, 20.2 mmol), Pd(PPh₃)₄ (0.58 g, 0.5 mmol) and potassium carbonate (4.2 g, 30 mmol) in dioxane/water (60 ml/10 ml) was degassed and heated at 95° C. overnight. After being cooled to RT, the mixture was filtered to collect the precipitate, which was redissolved in hot dichloromethane. The dichloromethane solution was filtered and concentrated with presence of methanol till large amount white precipitate forms. Filtration and drying in air gave a white solid 12 (2.58 g, in 60% yield).

Example 1.4.4

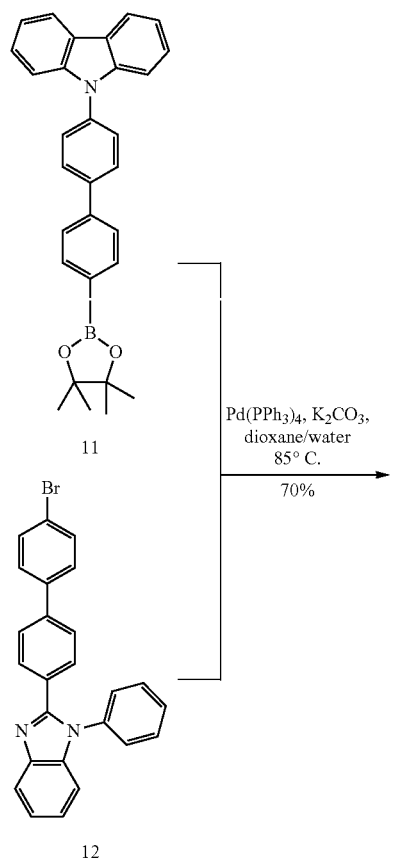

Host-4: A mixture of Compound 11 (1.34 g, 3.01 mmol), Compound 12 (1.28 g, 3.01 mmol), tetrakis(triphenylphosphine)palladium(0) (Pd(PPh$_3$)$_4$) (0.173 g, 0.15 mmol) and potassium carbonate (1.38 g, 10 mmol) in dioxane/water (80 ml/16 ml) was degassed and heated at 85° C. overnight. After being cooled to RT, the mixture was poured into dichoromethane (30 ml), then washed twice with brine. The organic phase was collected and concentrated to cause precipitation. The suspension was filtered and the solid and the filtrate were collected separately and loaded on silica gel and purified by flash column (dichloromethane to dichloromethane/ethyl acetate 10:1) to give white solid Host-4 (1.40 g, in 70% overall yield). LCMS data: calcd for $C_{49}H_{34}N_3$ (M+H): 664.3. found: m/e=664.

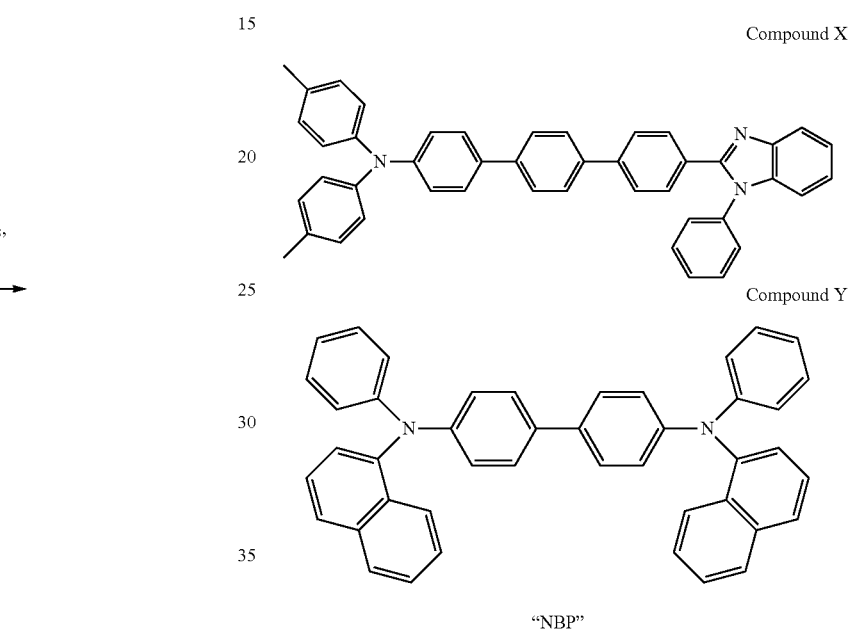

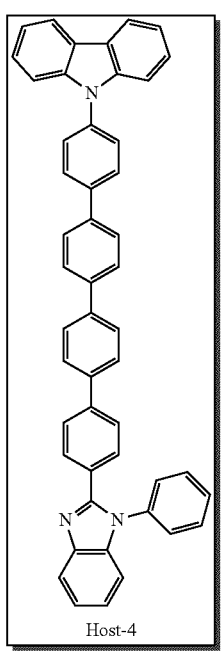

Example 2

OLED Device Configuration and Performance

Example 2.1

Device-A

Fabrication of Light-Emitting Device:

A device (Device A) was fabricated in a manner similar to the following. The ITO substrates having sheet resistance of about 14 ohm/sq were cleaned ultrasonically and sequentially in detergent, water, acetone, and then isopropyl alcohol (IPA); and then dried in an oven at 80° C. for about 30 min under an ambient environment. Substrates were then baked at about 200° C. for about 1 hour in an ambient environment, then under UV-ozone treatment for about 30 minutes. PEDOT: PSS (hole-injection material) was then spin-coated on the annealed substrate at about 4000 rpm for about 30 sec. The coated layer was then baked at about 100° C. for 30 min in an ambient environment, followed by baking at 200° C. for 30 min inside a glove box (N$_2$ environment). The substrate was then transferred into a vacuum chamber, where 4,4'-bis[N-(naphthyl)-N-phenyl-amino]biphenyl (NPB) was vacuum deposited at a rate of about 0.1 nm/s rate under a base pressure of about 2×10$^{-7}$ torr. Bis(1-phenylisoquinoline)(acetylacetonate)iridium (III) ("Ir(piq)$_2$acac") (10 wt %) was co-deposited as an emissive layer with Host-2 host material at about 0.01 nm/s and about 0.10 nm/s, respectively, to make the appropriate thickness ratio.

1,3,5-Tris(1-phenyl-1H-benzimidazol-)$_2$-yl)benzene (TPBI) was then deposited at about 0.1 nm/s rate on the emissive layer. A layer of lithium fluoride (LiF) (electron injection material) was deposited at about 0.005 nm/s rate followed by deposition of the cathode as Aluminium (Al) at about 0.3 nm/s rate. The representative device structure was: ITO (about 150 nm thick)/PEDOT:PSS (about 30 nm thick)/ NPB (about 40 nm thick)/Host-2: Ir(piq)$_2$acac (about 30 nm thick)/TPBI (about 30 nm thick)/LiF(about 0.5 nm thick)/Al (about 120 nm thick). The device was then encapsulated with a getter attached glass cap to cover the emissive area of the OLED device in order to protect from moisture, oxidation or mechanical damage.

Each individual device had an area of about 12 mm$^2$.

Example 2.2

Devices-B and -C

Other devices were constructed in accordance to Example 2,1, except that instead of Ir(piq)$_2$acac, bis(phenylquinoline) iridium acetylacetonate (Ir(PQ)$_2$acac) (6 wt %) was used as the emitting complex, which emits peak wavelength at 600 nm, with the respective host material; and the ITO thickness was 55 nm instead of 150. The deposition rate of emitter and host were 0.006 nm/s and 0.1 nm/s, respectively.

The representative device structures for Devices B and C was: ITO (about 55 nm thick)/PEDOT:PSS (about 30 nm thick)/NPB (about 40 nm thick)/Host-2 or Host-1/: Ir(PQ)$_2$ acac (about 30 nm thick)/TPBI (about 40 nm thick)/LiF (about 0.5 nm thick)/Al (about 120 nm thick). Each respective device was measured inside a glove box filled with nitrogen without encapsulation Each individual device had an area of about 9 mm$^2$.

Example 2.3

Other devices (Device D [Host-3], Device E [Host-4], Comparative Device X [Host-X], and Comparative Device Y [NPB]) were constructed in accordance to Example 2.2, except that instead of a mixture of Compound Host-1 (94%), and bis(2-phenyl quinolyl-N,C2')acetylacetonate iridium (III) (Ir(PQ)$_2$acac) (6%), a mixture of Compound Host-3 (94%), and bis(2-phenyl quinolyl-N,C2')acetylacetonate iridium(III) (Ir(PQ)$_2$acac), Compound Host-4 (94%), and bis (2-phenyl quinolyl-N,C2')acetylacetonate iridium(III) (Ir (PQ)$_2$acac), Comparative Compound X, 4'''-(1-phenyl-1H-benzo[d]imidazol-2-yl)-N,N-di-p-tolyl-[1,1':4',1''-terphenyl]-4-amine (94%), and bis(2-phenyl quinolyl-N,C2') acetylacetonate iridium(III) (Ir(PQ)$_2$acac) (6%), and Comparative Compound Y, 4,4'-bis[N-(naphthyl)-N-phenyl-amino]biphenyl (NPB) (94%), and bis(2-phenyl quinolyl-N, C2')acetylacetonate iridium(III) (Ir(PQ)$_2$acac) (6%) were co-deposited on top of NPB, respectively, to form a 30 nm thick light-emitting layer 20.

Each individual device had an area of about 9 mm$^2$.

Example 3

Device Performance

Example 3.1

All spectra were measured with an PR670, and I-V-L characteristics were taken with a Keithley 2400 SourceMeter (Keithley Instruments, Inc., Cleveland, Ohio, USA). All device operation was performed inside a nitrogen-filled glove-box.

Figure 7:
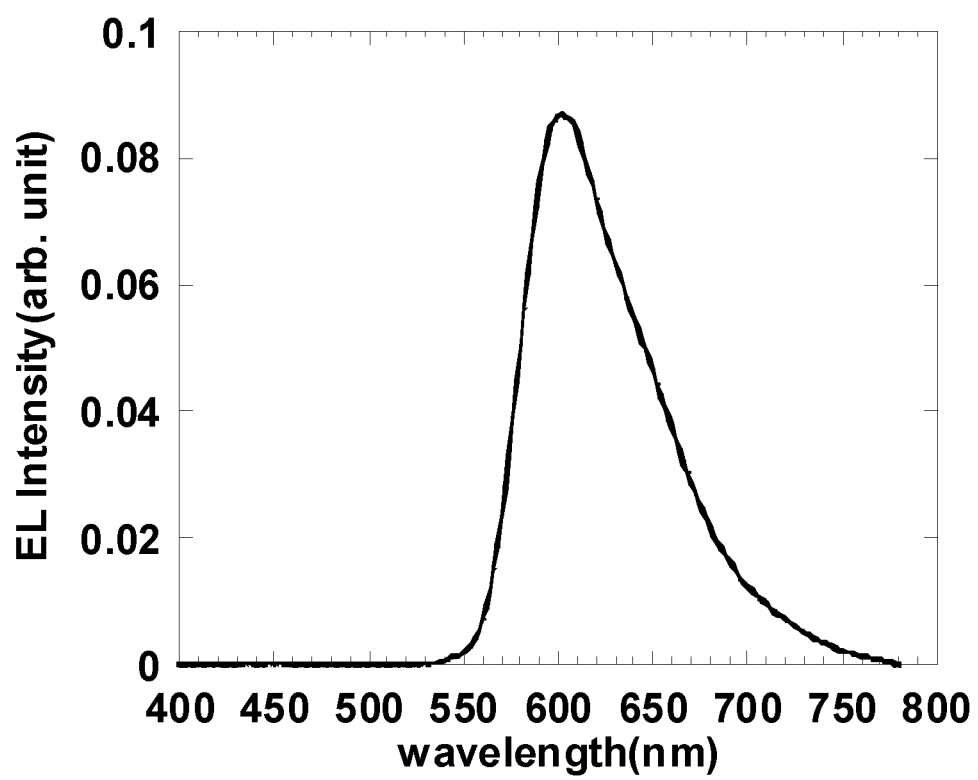
FIG. 7 is the electroluminescence spectrum of one embodiment of a light emitting device.
Figure 8:
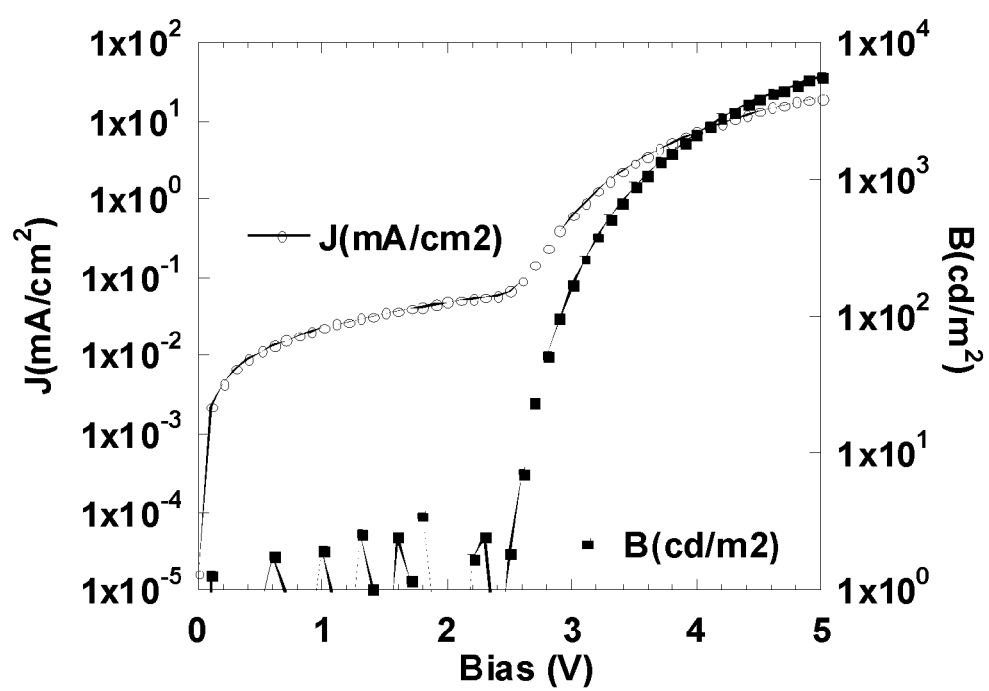
FIG. 8 is a current density/brightness vs. voltage curve of an embodiment of a light emitting device.
Figure 9:
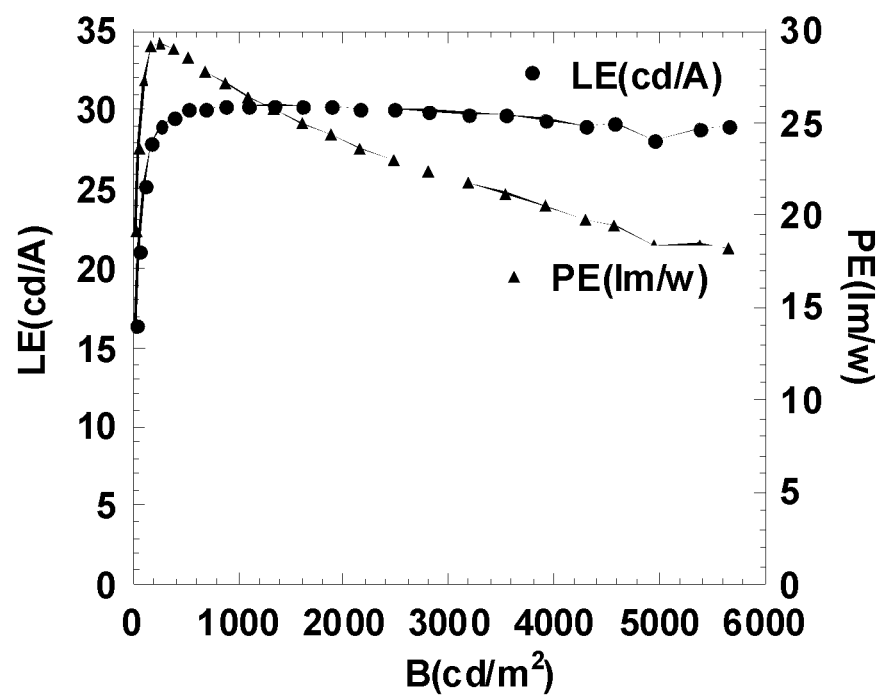
FIG. 9 shows the power efficiency and the luminescence efficiency with respect to the brightness ($cd/m^2$) of an embodiment of a light-emitting device.
Figure 10:
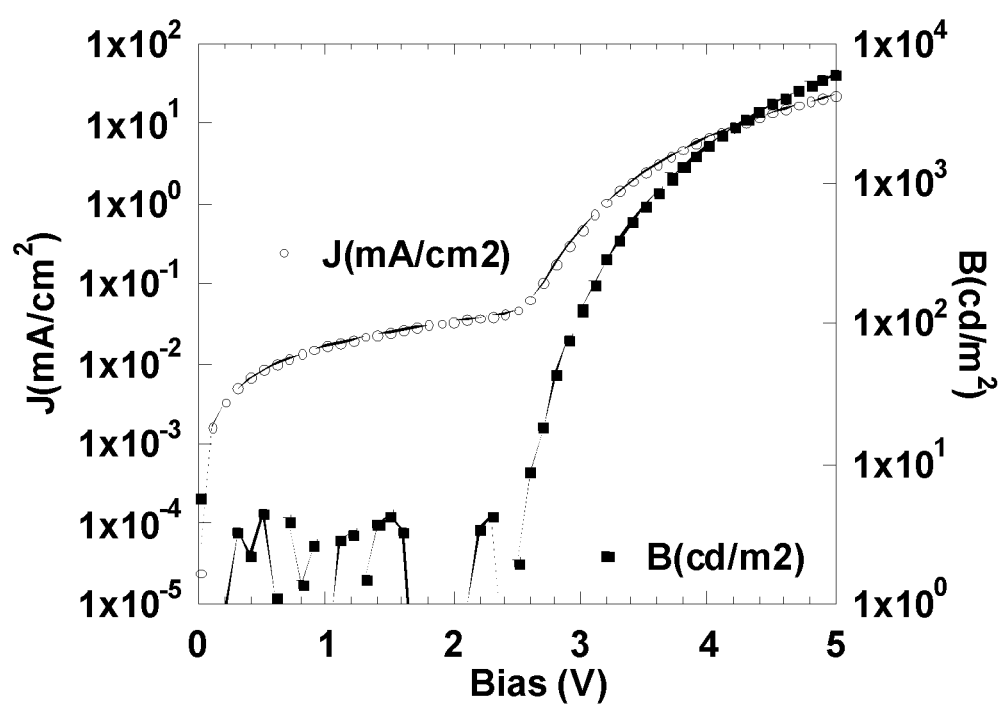
FIG. 10 is a current density/brightness vs. voltage curve of an embodiment of a light emitting device.
Figure 11:
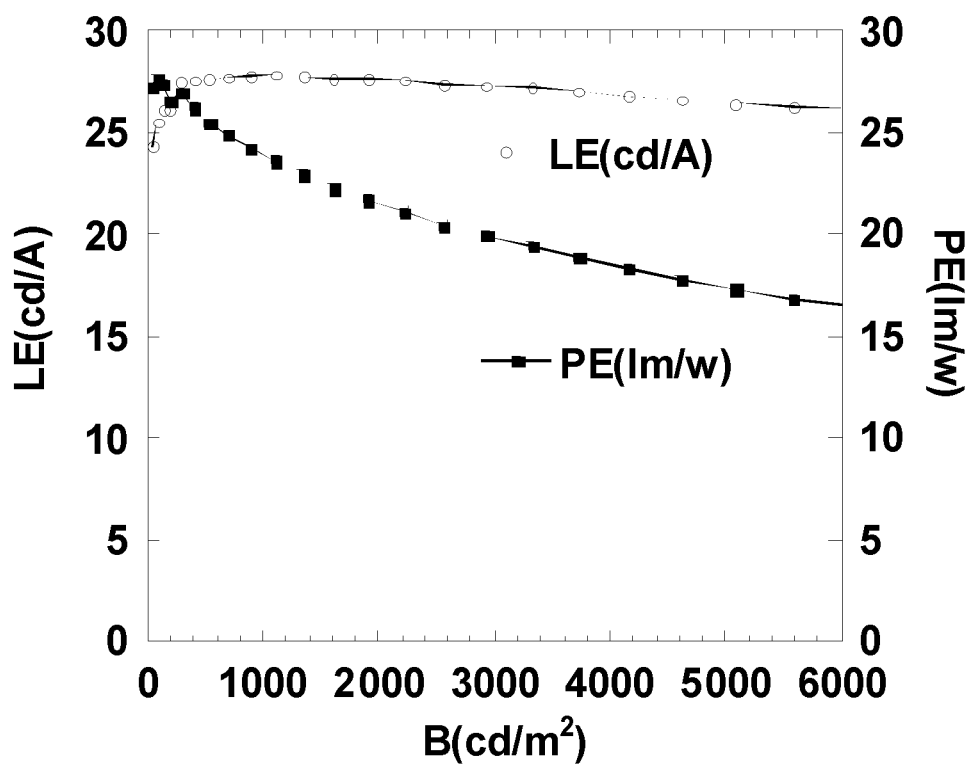
FIG. 11 shows the power efficiency and the luminescence efficiency with respect to the brightness ($cd/m^2$) of an embodiment of a light emitting device.

Device A, a red light emitting device, comprising Host-2: Ir(piq)$_2$acac and fabricated in accordance with Examples 1 and 2, was tested to determine the emissive qualities of the device by examining the current density and luminance as a function of the driving voltage, as shown in FIG. 2-6. The turn-on voltage for the device was about 2.5 volts and the maximum luminance was about 39,700 cd/m$^2$ with 12 mm$^2$ area device at about 8V. The EQE (external quantum efficiency), luminous efficiency and power efficiency of the device at 1000 cd/m$^2$ were about 15.5%, 12.3 cd/A and 10.4 μm/w at 630 nm emission. Device B and C, red light emitting devices, comprising Host-2: Ir(PQ)$_2$acac and Host-1: Ir(PQ)$_2$ acac, respectively, and fabricated in accordance with Examples 1 and 2. FIG. 7 is the electroluminescence spectrum of Device B. Devices B and C were tested to determine the emissive qualities of the device by examining the current density and luminance as a function of the driving voltage, as shown in FIG. 8-13. The turn-on voltage for the 9 mm$^2$ area device was about 2.5 volts The EQE (external quantum efficiency), luminous efficiency and power efficiency of Device B at 1000 cd/m$^2$ were about 16.2%, 30.3 cd/A and 26.6 μm/w for a device with a light emitting layer of Host-2:Ir(PQ)$_2$ acac(6 wt %) and EQE=15.4%, LE=27.8cd/A, PE=241 m/w for device with a light emitting layer of Host-1:Ir(PQ)$_2$acac(6 wt %) (Device C). Table 1 shows the respective device's power efficiency and luminescent efficiency of devices fabricated in accordance to examples 2,1, 2.2 and 2.3.

| Device | PE (Lm/w) | LE (cd/A) |
| --- | --- | --- |
| Device A | 10.4 | 12.3 |
| Device B | 24 | 27.8 |
| Device C | 26.6 | 30.3 |
| Device D | 32.8 | 35.6 |
| Device E | 5.83 | 9.29 |
| Device X | 28 | 30.9 |
| Device Y | 4.44 | 5.51 |

Thus Compounds Host-1 and Host-2 have demonstrated their effectiveness host materials in organic light emitting devices.

Example 3.2

Devices B and C, light emitting devices comprising Host-2: Ir(PQ)$_2$acac, and Host-1:Ir(PQ)$_2$acac, respectively, and fabricated in accordance with Examples 2.2, were tested to determine the lifetime of the devices (T$_{50}$(h) at 5000 nit). All spectra were measured with an PR670 and I-V-L characteristics were taken with a Keithley 2400 SourceMeter (Keithley Instruments, Inc., Cleveland, Ohio, USA). All device operation was performed inside a nitrogen-filled glove-box without encapsulation.

Table 2 shows the device lifetime of devices fabricated in accordance to Examples 2.1, 2.2 and 2.3.

| Device | T50(h) @ 5000 nit |
| --- | --- |
| Device A | 1150 |
| Device B | 1000 |
| Device C | 700 |
| Device D | 80 |

-continued

| Device | T50(h) @ 5000 nit |
|---|---|
| Device E | 200 |
| Comparative Device X | 36 |
| Comparative Device Y | 1.3 |

Thus at least Host-1 and Host-2 have demonstrated their effectiveness as a long lasting compound in light emitting organic light emitting devices.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A light-emitting device comprising a compound represented by a formula:

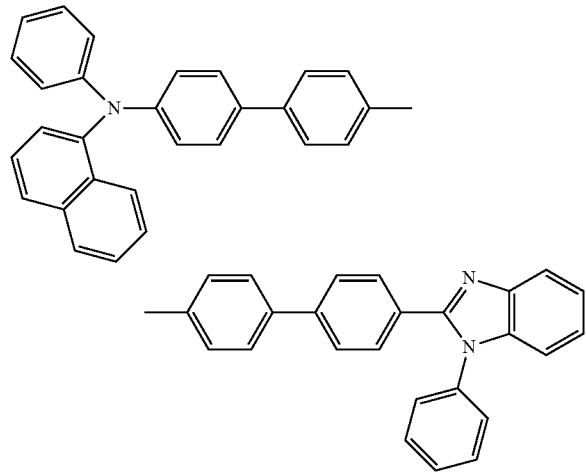

wherein the compound is a host in a light-emitting layer, and
wherein the light-emitting layer further comprises:

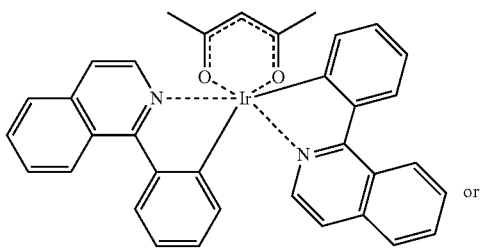

or

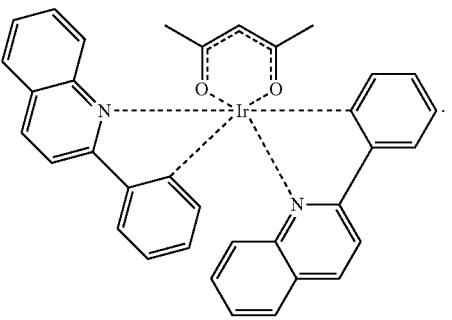

2. The light-emitting device of claim 1, further comprising a hole-transport layer disposed between the light-emitting layer and an anode.

3. The light-emitting device of claim 1, further comprising an electron-transport layer disposed between the light-emitting layer and a cathode.

* * * * *

UNITED STATES PATENT AND TRADEMARK OFFICE
CERTIFICATE OF CORRECTION

PATENT NO. : 8,426,040 B2
APPLICATION NO. : 13/033473
DATED : April 23, 2013
INVENTOR(S) : Shijun Zhen et al.

It is certified that error appears in the above-identified patent and that said Letters Patent is hereby corrected as shown below:

On the title page, item [75] in the listing of inventors, add Qianxi Lai, Sazzadur Rhaman Kahn, Sheng Li, Brett T. Harding, Hyunsik Chae, Rebecca Romero, and David T. Sisk as inventors, as follows:

-- Shijun Zheng
   Liping Ma
   Amane Mochizuki
   Qianxi Lai
   Sazzadur Rhaman Khan
   Sheng Li
   Brett T. Harding
   Hyunsik Chae
   Rebecca Romero
   David T. Sisk --

Signed and Sealed this
Twenty-ninth Day of October, 2013

Teresa Stanek Rea
*Deputy Director of the United States Patent and Trademark Office*